United States Patent
Cannavo et al.

(10) Patent No.: US 11,235,029 B2
(45) Date of Patent: Feb. 1, 2022

(54) METHODS FOR TREATING HEART FAILURE WITH A TRKB AGONIST

(71) Applicants: Temple University-Of The Commonwealth System of Higher Education, Philadelphia, PA (US); Johns Hopkins Technology Ventures, Baltimore, MD (US); Universita di Napoli Federico II, Naples (IT)

(72) Inventors: Alessandro Cannavo, Naples (IT); Ning Feng, Wexford, PA (US); Giuseppe Rengo, Naples (IT); Nazareno Paolocci, Baltimore, MD (US); Walter J. Koch, Malvern, PA (US)

(73) Assignees: Temple University-Of The Commonwealth System of Higher, Philadelphia, PA (US); Education Johns Hopkins Technology Ventures, Baltimore, MD (US); Universita di Napoli Federico II, Naples (IT)

( * ) Notice: Subject to any disclaimer, the term of this patent is extended or adjusted under 35 U.S.C. 154(b) by 0 days.

(21) Appl. No.: 15/916,494

(22) Filed: Mar. 9, 2018

(65) Prior Publication Data

US 2018/0256683 A1 Sep. 13, 2018

Related U.S. Application Data

(60) Provisional application No. 62/469,287, filed on Mar. 9, 2017.

(51) Int. Cl.
| | | |
|---|---|---|
| *A61K 38/18* | (2006.01) | |
| *A61K 31/166* | (2006.01) | |
| *A61K 31/353* | (2006.01) | |
| *A61K 31/404* | (2006.01) | |
| *A61K 31/138* | (2006.01) | |
| *A61P 9/04* | (2006.01) | |
| *C07K 14/71* | (2006.01) | |
| *C07K 14/475* | (2006.01) | |
| *A61K 39/00* | (2006.01) | |

(52) U.S. Cl.
CPC .......... *A61K 38/185* (2013.01); *A61K 31/138* (2013.01); *A61K 31/353* (2013.01); *A61K 31/404* (2013.01); *A61P 9/04* (2018.01); *A61K 31/166* (2013.01); *A61K 2039/505* (2013.01); *C07K 14/475* (2013.01); *C07K 14/71* (2013.01)

(58) Field of Classification Search
CPC .. A61K 31/138; A61K 38/185; A61K 31/166; A61K 31/353; A61K 31/404; A61P 9/04
See application file for complete search history.

(56) References Cited

U.S. PATENT DOCUMENTS

2010/0305213 A1  12/2010  Beddies

FOREIGN PATENT DOCUMENTS

WO    WO-2016112012 A1 *  7/2016  .......... A61K 38/185

OTHER PUBLICATIONS

Feng et al, 2013. Circulation. vol. 128, No. 22, Suppl. 1, Abstract No. 16549 (Year: 2013).*
DeAlmeida et al, 2010. Journal of Visualized Experiments. 38: 1-3.*
Feng et al., "Constitutive BDNF/TrkB signaling is required for normal cardiac contraction and relaxation," Proc Natl Acad Sci USA. 2015; 112:1180-1885.
Huang et al., "G protien-coupled receptor kinases in normal and failing myocardium," Front Biosci (Landmark Ed). 2011 ; 16: 3047-3060.
Chen, MJ et al., "Norepinephrine induces BDNF and activates the PI-3K and MAPK cascades in embryonic huppocampal nuerons," Cell Signal. 2007; 19:114-128.
Chen, R et al., "Cardiac BDNF/TrkBSignaling Can Be Induced By Calorie Restriction With Imporoved Physcial Activity in Obese Mice," The Internet Journal of Cardiovascular Research, 2013, vol. 8:1, 6 pages.
Finkbeiner et al., "CREB: A Major Mediator of Neuronal Neurotrophin Responses," Neuron. 1997; 19: 1031-104.
Hoard JL et. al, "Cholinergic neurons of mouse intrinsic cardiac ganglia contain noradrenergic enzymes, norepinephrine transporters, and the neurotrophin receptors TrkA and p75," Neuroscience. 2008 156: 129-142.
Massa et al., "Small molecule BDNF mimetics activate TrkB signaling and prevent neuronal degeneration in rodents," J Clin Invest. 2010;120(5):1774-1785.
Parker D et al., "Phosphorylation of CREB at Ser-133 Induces Complex Formation with CREB-Binding Protien via a Direct Mechanism," Mol Cell Biol. 1996: 16: 694-703.

* cited by examiner

*Primary Examiner* — Zachary C Howard
(74) *Attorney, Agent, or Firm* — Riverside Law LLP

(57) ABSTRACT

The present invention relates to compositions and methods for the treatment of heart failure.

4 Claims, 12 Drawing Sheets

METHODS FOR TREATING HEART FAILURE WITH A TRKB AGONIST

CROSS-REFERENCE TO RELATED APPLICATIONS

This application claims priority from U.S. Provisional Application Ser. No. 62/469,287, filed Mar. 9, 2017, the contents of which are incorporated by reference herein in its entirety.

STATEMENT REGARDING FEDERALLY SPONSORED RESEARCH OR DEVELOPMENT

This invention was made with government support under grant Nos. R37-HL061690 and P01-HL025443 awarded by the National Institutes of Health. The Government has certain rights in the invention.

BACKGROUND OF THE INVENTION

Heart failure may be described as the inability of the heart to adequately pump blood throughout the body, and is among the leading causes of death in industrialized countries; it is characterized by the desensitization of G protein-coupled receptor (GPCR) signaling, particularly the β-adrenergic receptor (βAR) system (Huang, Z M et al. Front Biosci (Landmark Ed). 2011; 16:3047-60). β-1 adrenergic receptor (β-1 AR) stimulation and β-2 adrenergic receptor (β-2 AR) stimulation are essential to adjust cardiac force generation in the presence of physiological stress (i.e., exercise) or pathological hemodynamic stress (Huang, Z M et al. Front Biosci (Landmark Ed). 2011; 16:3047-60). However, the long-term use of βAR agonists in the failing heart generates catecholamine toxicity, and instead, βAR antagonists (βAR-blockers) can improve mortality and function of the failing heart (Huang, Z M et al. Front Biosci (Landmark Ed). 2011; 16:3047-60). For example, U.S. Patent Application Publication 2010/0305213 A1 (Beddies et al.) relates to a method of reversing cardiac remodeling of animals with a pathological cardiac disorder by administering to the animal in need thereof a β-blocker. While phasic control of myocardial function by βAR signaling is certainly important for the normal heart, modulation of alternative pathways may provide additional therapeutic benefits.

Brain-derived neurotrophic factor (BDNF) induces a more "tonic" influence on myocardial function by specifically binding to its specific sarcolemmal tyrosine kinase B receptor, TrkB (Feng, N et al. Proc Natl Acad Sci USA. 2015; 112:1880-5). Cardiac BDNF/TrkB signaling can be induced by calorie restriction and improved physical activity in obese mice, with beneficial effects (Chen, R et al. The Internet Journal of Cardiovascular Research, 8:1), while deleting cardiac TrkB results in a marked reduction in both basal cardiac contraction and relaxation (Feng, N et al. Proc Natl Acad Sci USA. 2015; 112:1880-5). It has been suggested that β-1 and β-2 AR stimulation can promote BDNF production in neurons (Chen, M J et al. Cell Signal. 2007; 19:114-28), but whether BDNF is released from myocytes is unknown. Similarly, the importance of any autologous production of BDNF in myocytes, and its regulation by βAR signaling in the pathophysiology of heart failure also remains unknown.

Thus, there remains a need in the art for an improved understanding of the pathways affecting the failing heart, especially the BDNF/TrkB pathway, and for therapies that utilize these pathways in a beneficial manner. The present invention, compositions and methods for treating heart failure by administering a BDNF or TrkB agonist in combination with βAR-blockers, addresses this unmet need.

SUMMARY OF THE INVENTION

In one aspect, the invention provides a composition for treating or preventing heart failure in a subject in need thereof. In one aspect, the composition comprises at least one selected from the group consisting of BDNF, a TrkB agonist, and a βAR-blocker.

In various embodiments, BDNF is at least one selected from the group consisting of full-length BDNF, a functional fragment of BDNF, an analog of BDNF, and a derivative of BDNF.

In various embodiments, the TrkB agonist is at least one selected from the group consisting of N,N',N"-tris(2-hydroxyethyl)-1,3,5-benzenetricarboxamide (LM22A-4), a functional fragment of LM22A-4, an analog of LM22A-4, a derivative of LM22A-4, 7,8-dihydroxyflavone, an analog of 7,8-dihydroxyflavone, and a derivative of 7,8-dihydroxyflavone.

In various embodiments, the TrkB agonist is at least one selected from the group consisting of an antibody and an antibody fragment.

In various embodiments, the TrkB agonist is at least one selected from the group consisting of a vector encoding TrkB, a vector encoding a dominant negative isoform of GRK2, and a vector encoding an antisense nucleic acid molecule targeting GRK2.

In one embodiment, the βAR-blocker is an βAR-antagonist, $\beta_2$AR-antagonist, $\beta_3$AR-antagonist, or any combination thereof. For example, in one embodiment, the βAR-blocker is selective for $\beta_1$AR. In one embodiment, the βAR-blocker is selective for $\beta_2$AR. In one embodiment, the βAR-blocker is selective for $\beta_3$AR.

In various embodiments, the βAR-blocker is at least one selected from the group consisting of Bisoprolol, Carvedilol, Carvedilol phosphate, Metoprolol Succinate, Nebivolol, a functional fragment of Bisoprolol, a functional fragment of Carvedilol, a functional fragment of Carvedilol phosphate, a functional fragment of Metoprolol Succinate, a functional fragment of Nebivolol, an analog of Bisoprolol, an analog of Carvedilol, an analog of Carvedilol phosphate, an analog of Metoprolol Succinate, an analog of Nebivolol, a derivative of Bisoprolol, a derivative of Carvedilol, a derivative of Carvedilol phosphate, a derivative of Metoprolol Succinate, and a derivative of Nebivolol.

In one aspect, the invention provides a method of treating or preventing heart failure in a subject in need thereof. In one aspect, the method comprises administering to the subject a therapeutically effective amount of a composition comprising at least one selected from the group consisting of BDNF, a TrkB agonist, and a βAR-blocker.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4, comprising FIG. 4A depicts immunoblots for GRK2, BDNF, and GAPDH, taken from left ventricle tissue of control non-transgenic (NLC) mice. Four weeks after induced myocardial infarction (MI), the analysis revealed that GRK2 was slightly, but not significantly upregulated after 24 hours following MI, whereas it was markedly elevated 4 weeks after the initial ischemic event. In parallel, cardiac BDNF expression was significantly elevated 24 hours after MI (when GRK2 was not significantly affected), but it plummeted to basal (pre-MI) values 4 weeks after MI when GRK2 peaked instead. FIG. 4B depicts echocardiographic analyses (ejection fraction (EF), left ventricular end systolic dimension (LVESD)) of mouse hearts and serum levels of BDNF (BDNF serum) in control non-transgenic (NLC) mice (green bars) and in cardiac-specific GRK2 overexpressing mice (GRK2$^{tg}$) (red bars), taken 4 weeks after either MI or sham (control). GRK2$^{tg}$ mice presented with more severe cardiac dysfunction and adverse remodeling compared to NLC mice at 4 weeks after MI when chronic cardiac decompensation ensues. Moreover, whereas circulating BDNF levels increased in control (NCL) infarcted mice, serum BDNF was not elevated after MI in GRK2 transgenic (GRK2$^{tg}$) mice. FIG. 4C depicts immunoblots for GRK2, BDNF, and GAPDH, taken from left ventricle tissue of control non-transgenic (NLC) mice or GRK2$^{tg}$ mice 4 weeks following sham or MI. Importantly, BDNF was persistently elevated 4 weeks after MI in control (NLC) infarcted mice, but it dropped dramatically in infarcted GRK2$^{tg}$ mice in which GRK2 remained persistently elevated even after infarction.

FIG. 6, comprising FIG. 6A, FIG. 6B and FIG. 6C depict sham WT MI and GRK2$^{tg}$ staining of planar sections of mouse left ventricle (LV) for tyrosine hydroxylase (TH), a marker of noradrenergic neurons (Melchitzky D S et al. Neuropsychopharmacology. 2000; 22:466-72 and Hoard J L, et al. Neuroscience. 2008; 156:129-42), and GAP-43, an integral membrane protein associated with the cytoplasmic surface of axonal growth cones (and thus with axonal growth). In control (NLC) mice, myocardial infarction led to a marked reduction in both TH and GAP-43 staining. FIG. 6D depicts quantification of TH staining. FIG. 6E depicts quantification of GAP43 staining.

FIG. 7, comprising FIG. 7A depicts rescue of cardiac defects following MI resulting from chronic infusion of LM22A-4, a specific agonist of TrkB (Massa S M, et a. J Clin Invest. 2010; 120:1774-85) at 0.2 mg/kg/day in saline, started 1 week after MI. The treatment prevented LV dysfunction and adverse remodeling 4 weeks after severe MI: % EF was 10.46±2.3 in untreated (vehicle treated) infarcted mice vs. 23.3±2.1 in LM22A-4 treated animals, while LVDs was 7.4±0.05 vs. 6.1±0.25 mm. FIG. 7B depicts cardiac tissue sections and quantitation of fibrosis observed in sham, MI, and MI+LM22A-4 groups. Compared to the MI group without treatment, fibrosis was lower in TrkB agonist-treated hearts. FIG. 7C depicts immunoblots for BDNF and GAPDH from lysates taken from isolated control myocytes treated with NS, Iso, LM22A, or β3 agonist BRL 37344 (BRL). As shown, treatment with LM22A-4 induced myocardial BDNF in isolated control myocytes.

DETAILED DESCRIPTION

Figure 1:
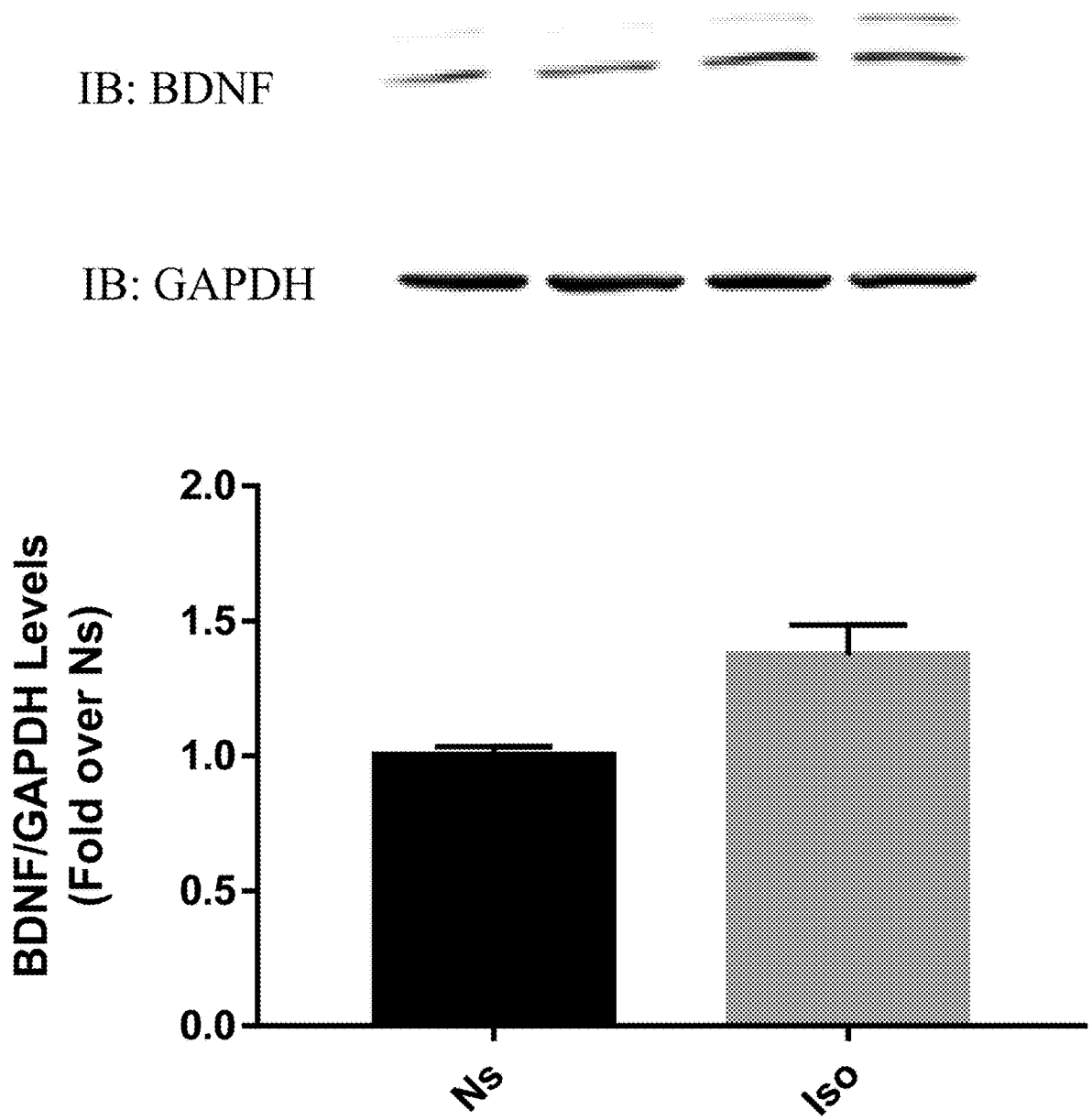
FIG. 1 depicts immunoblots for BDNF and GAPDH, taken from neonatal rat ventricular cardiomyocytes (NRVMs). NRVMs were infected with an Adenovirus (Ad) encoding for LacZ (control for data presented in FIG. 2). Infected NRVMs were stimulated for 12 hours with (Iso) or without (non-stimulated, Ns) the βAR agonist Isoproterenol (ISO, 5 nM) prior to harvesting for immunoblot analysis. ISO stimulation of Ad-Lacz (control) cells resulted in a significant increase of BDNF expression levels (~1.3-fold, n=3) compared to non-stimulated (Ns) control cells.

The present invention provides in part compositions and methods for treating heart failure using an agonist of TrkB and/or BDNF in combination with a βAR blocker. The invention relates to the discovery that in addition to TrkB stimulation, myocardial BDNF production is regulated by βAR signaling, and that, in the injured heart, normal βAR signaling is required for adequate BDNF generation and BDNF-induced protection against acute or chronic hemodynamic stress. Moreover, myocardial BDNF generation is sensitive to the levels of the major βAR inhibitory kinase, GRK2, wherein low levels of GRK2 lead to higher myocardial BDNF content. Without wishing to be bound by any particular theory, it is believed that the novel cardiac βAR/BDNF/TrkB system identified herein demonstrates that the lower BDNF production due to βAR desensitization/GRK2 upregulation in failing hearts plays a key role in the contribution of chronic βAR dysfunction in disease progression. This evidence highlights the therapeutic relevance of GRK2 inhibitors that are predicted to increase myocardial BDNF content in diseased hearts, either after myocardial infarction or in another acute or chronic cardiac disease in which the βAR system is altered. The results presented herein also show for the first time that selective and specific Trk agonists such as LM22A-4 directly enrich the myocardium with BDNF and prevent HF progression in infarcted mice with a mechanism that, at least in part, involves eNOS stimulation. Therefore, in one embodiment, the present invention provides a therapy for heart failure in which a BDNF and/or TrkB agonist is combined with a βAR blocker to improve cardiac function.

In one embodiment, the invention provides a composition comprising BDNF, a TrkB agonist, βAR-blocker, or a combination thereof.

In one embodiment, the invention provides a composition comprising at least one agent that directly or indirectly modulates the amount or activity of BDNF, a TrkB agonist, βAR-blocker, or a combination thereof. In one embodiment, the composition comprises an inhibitor of a negative regulator of BDNF, an inhibitor of a negative regulator of a TrkB agonist, an inhibitor or a negative regulator of a βAR-blocker, or a combination thereof. In one embodiment, the composition comprises an activator of a positive regulator of BDNF, an activator of a positive regulator of a TrkB agonist, an activator of a positive regulator of a βAR-blocker, or a combination thereof.

In one embodiment, the invention provides a method for treating a cardiovascular disease or disorder in a subject comprising administering a composition comprising BDNF, a TrkB agonist, βAR-blocker, or a combination thereof in a subject in need thereof.

In one embodiment, the invention provides a method for treating a cardiovascular disease or disorder in a subject comprising administering a composition comprising at least one agent that directly or indirectly modulates the amount or activity of BDNF, a TrkB agonist, βAR-blocker, or a combination thereof.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

The term "analog" as used herein generally refers to compounds that are generally structurally similar to the compound of which they are an analog, or "parent" compound. Generally, analogs will retain certain characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, more preferably at least about 80%-85% or about 86%-89%, and still more preferably at least about 90%, about 92%, about 94%, about 96%, about 98% or about 99% of the amino acids in a given amino acid sequence of the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function. As applied to polynucleotides, the term "analog" may have varying ranges of nucleic acid sequence identity to the parent compound, for example at least about 70%, more preferably at least about 80%-85% or about 86%-89%, and still more preferably at least about 90%, about 92%, about 94%, about 96%, about 98% or about 99% of the nucleic acids in a given nucleic acid sequence of the parent or a selected portion or domain of the parent. As applied to polynucleotides, the term "analog" generally refers to polynucleotides which are comprised of a segment of about at least 9 nucleic acids that has substantial identity to at least a portion of the parent. Analogs typically are at least 15 nucleic acids long, at least 60 nucleic acids long or longer, at least 150 nucleic acids long or longer, at least 300 nucleic acids long or longer, at least 450 nucleic acids long or longer, at least 600 nucleic acids long or longer, and more typically at least 750 nucleic acids long or longer. Some analogs may lack substantial biological activity but may still be employed for various uses, such as for encoding epitopes for raising antibodies to predetermined epitopes, as a reagent to detect and/or purify sequences by hybridization assays, or as a competitive or noncompetitive agonist, antagonist, or partial agonist of a target or modulator of a target.

The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "activating antibody" is an antibody that activates a target or a modulator of a target by at least about 20% when added to a cell, tissue or organism expressing the target or modulator of the target.

The term "antibody fragment" or "binding fragment" refers to at least one portion of an antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the binding specificity and neutralizing activity characteristic of the donor antibody.

The term "acceptor antibody" refers to an antibody (monoclonal and/or recombinant) heterologous to the donor antibody, which contributes all (or any portion, but in some embodiments, all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions (FR) on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

An "agonist of TrkB," as the term is used herein, refers to an agent which increases the biological activity of the receptor TrkB.

An "antisense nucleic acid molecule," as the term is used herein, refers to any one or more nucleic acid molecules having a sequence that is complementary to the sense sequence of a molecule of mRNA, the target of the antisense nucleic acid molecule. Antisense nucleic acid molecules act by interfering with the function or activity of their target mRNA molecule.

A "dominant negative isoform" of a target, for example, GRK2, as the term is used herein, refers to a mutant of a target that, when present in a cell, abolishes or decreases the function or activity of the simultaneously-expressed wild-type target.

A "βAR-blocker," as the term is used herein, refers to any one or more antagonists of any one or more of the β-adrenergic receptors. In one embodiment, the βAR-blocker is an $β_1$AR-antagonist, $β_2$AR-antagonist, $β_3$AR-antagonist, or any combination thereof. For example, in one embodiment, the βAR-blocker is selective for $β_1$AR. In one embodiment, the βAR-blocker is selective for $β_2$AR. In one embodiment, the βAR-blocker is selective for $β_3$AR. βAR-blockers are known in the art, and are described, for example, in Helfand, M et al. Drug Class Review: Beta Adrenergic Blockers. Final Report. Update 4. July 2009. Oregon Health and Science University.

As used herein, the term "neutralizing" may refer to neutralization of biological activity of a target when a binding molecule specifically binds the target. In the context of the β-adrenergic receptors, a neutralizing binding molecule is a βAR-blocker, the binding of which to βAR results in inhibition of a biological activity of βAR. Preferably the neutralizing binding molecule binds βAR and reduces a biological activity of βAR by at least about 20%, 40%, 60%, 80%, 85% or more. In some embodiments, the βAR is human βAR.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

As used herein, the terms "congestive heart failure, (CHF)" "chronic heart failure," "acute heart failure," and "heart failure" are used interchangeably, and refer to any condition in which the heart is unable to adequately pump blood. When the heart is unable to adequately pump blood to the rest of the body at normal filling left ventricular pressures, blood can back up into the lungs, causing the lungs to become congested with fluid. Typical symptoms of heart failure include shortness of breath (dyspnea), fatigue, weakness, difficulty breathing when lying flat, and swelling of the legs, ankles or abdomen (edema). Causes of heart failure are related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction.

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

The term "high affinity" for binding domain polypeptides described herein refers to a dissociation constant ($K_d$) of at least about $10^{-6}$M, preferably at least about $10^{-7}$M, more preferably at least about $10^{-8}$M or stronger, more preferably at least about $10^{-9}$M or stronger, more preferably at least about $10^{-10}$M or stronger, for example, up to $10^{-12}$ M or stronger. However, "high affinity" binding can vary for other binding domain polypeptides.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce the level of a molecule, a reaction, an interaction, a gene, an mRNA, and/or a protein's expression, stability, amount, function or activity by a measurable amount or to prevent production entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

The terms "modulator" and "modulation" of a molecule of interest, as used herein in its various forms, is intended to encompass antagonism, agonism, partial antagonism and/or partial agonism of an activity associated with the protein of interest. The terms "modulator" and "modulation" are used interchangeably with the terms "regulator" and "regulation," respectively. In various embodiments, "modulators" may inhibit or stimulate protein expression or activity. Such modulators include small molecules agonists and antagonists of a protein molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "vector," as used in the context of the present invention, refers to a DNA molecule used as a vehicle to carry genetic material into a cell or other host, where it can be replicated and/or expressed.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" it is meant, for example, a carrier, diluent or excipient that is compatible with the other ingredients of the formulation and generally safe for administration to a recipient thereof. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically, such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, preferably a mammal, and most preferably a human, having a complement system, including a human in need of therapy for, or susceptible to, a condition or its sequelae. Thus, the individual may include, for example, dogs, cats, pigs, cows, sheep, goats, horses, rats, monkeys, and mice and humans.

The phrase "percent (%) identity" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, including heart failure, or a subject who ultimately may acquire such a disease or disorder, including heart failure, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. With regard to a small molecule, "variant" refers to a small molecule that differs in structure from a reference small molecule, but retains essential biological properties of the reference small molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. Small molecule variants may be produced by chemistry methods generally available to those skilled in the art.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

DESCRIPTION

The present invention relates to the discovery that the administration of BDNF or TrkB agonists is an effective therapy for improving cardiac symptoms, structures, functions, and/or outcomes in patients with heart failure (HF). βAR-blockers are known to benefit many patients of HF. Thus, the invention relates to compositions and methods for treating or preventing HF in a subject by administering a composition which directly or indirectly modulates TrkB signaling and directly or indirectly modulates βAR signaling.

In one embodiment, the invention provides a composition which directly or indirectly modulates the amount or activity of BDNF, TrkB, βAR, or a combination thereof.

In one embodiment, the invention provides a composition which directly or indirectly agonizes TrkB signaling and directly or indirectly antagonizes βAR signaling.

In one embodiment, the invention provides a composition comprising BDNF, a TrkB agonist, βAR-blocker, or a combination thereof.

In one embodiment, the invention provides a method for treating a cardiovascular disease or disorder in a subject comprising administering a composition which directly or indirectly modulates the amount or activity of BDNF, TrkB, βAR, or a combination thereof.

In one embodiment, the invention provides a method for treating a cardiovascular disease or disorder in a subject comprising administering a composition which directly or indirectly agonizes TrkB signaling and directly or indirectly antagonizes βAR signaling.

In one embodiment, the invention provides a method for treating a cardiovascular disease or disorder in a subject comprising administering a composition comprising BDNF, a TrkB agonist, βAR-blocker, or a combination thereof to a subject in need thereof.

In some embodiments, the composition administered comprises BDNF, or a functional fragment, analog, or derivative thereof.

In some embodiments, the TrkB agonist comprises N,N', N"-tris(2-hydroxyethyl)-1,3,5-benzenetricarboxamide (LM22A-4) (Massa S M, et al. J Clin Invest. 2010; 120: 1774-85), or a functional fragment, analog, or derivative thereof.

The invention also relates to the discovery that βAR signaling activity in the heart regulates autologous production of BDNF. An increase in βAR signaling promotes BDNF, via activation of CREB, which exerts a protective effect on the heart by activation of TrkB signaling. However, the long-term use of βAR agonists in the failing heart generates catecholamine toxicity, and instead, βAR antagonists (βAR-blockers) can improve mortality and function of the failing heart (Huang, Z M et al. Front Biosci (Landmark Ed). 2011; 16:3047-60).

In some embodiments, the composition administered directly or indirectly modulates βAR signaling. In one embodiment, the modulator is an antagonist. In one embodiment, the antagonist comprises a βAR-blocker, or a functional fragment, analog, or derivative thereof.

The invention also relates to the discovery that cardiac BDNF is controlled by GRK2, which when present in high levels, reduces βAR signaling and, as a result, reduces the amount of BDNF.

In some embodiments, the composition administered directly or indirectly modulates the amount or activity of a regulator of BDNF. In one embodiment, the regulator of BDNF lowers the amount or activity of BDNF, and the modulator is an inhibitor of the regulator of BDNF. In one embodiment, the regulator of BDNF is GRK2. In one embodiment, the inhibitor comprises an antisense nucleic acid targeting GRK2, or a functional fragment, analog, or derivative thereof.

The invention also relates to the discovery that the administration of a TrkB agonist following a cardiac event such as myocardial infarction (MI) at least partially restores cardiac function (ejection fraction, EF) and structure (left ventricular end-diastolic dimension, LVEDD), promotes BDNF accumulation in the heart, and reduces cardiac fibrosis (FIG. 7). Therefore, the present invention relates to the discovery that the activation of TrkB signaling in the heart can be beneficial for HF patients.

Generally, HF is any condition characterized by abnormally low cardiac output in which the heart is unable to pump blood at an adequate rate or does so only in the presence of increased left ventricular filling pressures. The present invention provides compositions and methods related to the treatment and prevention of any condition which can be characterized as HF. HF can include a wide variety of symptoms treatable with the compositions and methods of the invention. In some embodiments, the HF comprises impaired left ventricular ejection fraction ("systolic" heart failure). In other embodiments, the HF is preserved ejection fraction (HFpEF, sometimes called "diastolic" heart failure). The present invention provides compositions and methods for modulating cardiac abnormalities in a subject diagnosed with HF. In various embodiments, the abnormalities treatable with the compositions and methods of the invention include impaired cardiac function, low cardiac BDNF levels, high cardiac fibrosis levels, and ventricular remodeling following a cardiac event, such as a myocardial infarction (MI).

Compositions

In one embodiment, the invention provides a composition comprising BDNF, a TrkB agonist, βAR-blocker, or a combination thereof. In one embodiment, the invention relates to a composition that increases BDNF, a TrkB agonist, βAR-blocker, or a combination thereof. In one embodiment, increases BDNF, a TrkB agonist, βAR-blocker, or a combination thereof includes but is not limited to the amount, expression, activity and the likes of BDNF, a TrkB agonist, βAR-blocker.

In various embodiments, the present invention includes compositions for modulating the level or activity of BDNF in a subject, a cell, a tissue, or an organ in need thereof. In various embodiments, the compositions of the invention increase the amount of BDNF polypeptide, the amount of BDNF mRNA, the amount of BDNF activity, or a combination thereof.

In various embodiments, the present invention includes compositions for modulating the level or activity of TrkB in a subject, a cell, a tissue, or an organ in need thereof. In various embodiments, the compositions of the invention increase the amount of TrkB polypeptide, the amount of TrkB mRNA, the amount of TrkB activity, or a combination thereof. In various embodiments, the present invention includes compositions for modulating the level or activity of TrkB agonist in a subject, a cell, a tissue, or an organ in need thereof. In various embodiments, the compositions of the invention increase the amount of TrkB agonist polypeptide, the amount of TrkB agonist mRNA, the amount of TrkB agonist activity, or a combination thereof.

In various embodiments, the present invention includes compositions for modulating the level or activity of βAR in a subject, a cell, a tissue, or an organ in need thereof. In one embodiment, the compositions of the invention modulate the level or activity of $\beta_1AR$ in a subject, a cell, a tissue, or an organ in need thereof. In one embodiment, the compositions of the invention modulate the level or activity of $\beta_2AR$ in a subject, a cell, a tissue, or an organ in need thereof. In one embodiment, the compositions of the invention modulate the level or activity of $\beta_3AR$ in a subject, a cell, a tissue, or an organ in need thereof.

In various embodiments, the compositions of the invention modulate the amount of βAR polypeptide, the amount of βAR mRNA, the amount of βAR activity, or a combination thereof. In one embodiment, the compositions of the invention selectively modulate the amount of $\beta_1AR$ polypeptide, the amount of $\beta_1AR$ mRNA, the amount of $\beta_1AR$ activity, or a combination thereof. In one embodiment, the compositions of the invention selectively modulate the amount of $\beta_2AR$ polypeptide, the amount of $\beta_2AR$ mRNA, the amount of $\beta_2AR$ activity, or a combination thereof. In one embodiment, the compositions of the invention selectively modulate the amount of $\beta_3AR$ polypeptide, the amount of $\beta_3AR$ mRNA, the amount of $\beta_3AR$ activity, or a combination thereof.

Agents that may be used in the invention include any agent that modulates BDNF, a TrkB agonist or βAR-blocker, or a regulator of BDNF, a regulator of a TrkB agonist, or a regulator of a βAR-blocker. For example, agents that may be used in the invention include, without limitation, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes). Agents may also comprise alcohols, alkyl halides, amines, amides, esters, aldehydes, ethers and other classes of organic agents.

Any agent that mimics, activates, stimulates, potentiates or increases the biological activity of BDNF is contemplated by the present invention. BDNF includes purified or recombinant nucleic acids that encode BDNF proteins or fragments thereof, purified or recombinant BDNF polypeptides or fragments thereof, or other agents that mimic, activate, stimulate, potentiate or increase the biological activity of BDNF.

Functional examples of BDNF include, without limitation, agents that increase BDNF mRNA or protein, agents that increase BDNF signaling activity, agents that increase interaction between BDNF and its receptor TrkB (e.g., bivalent antibodies that bind TrkB and BDNF, fusion proteins with CDR combinations that bind TrkB and BDNF), and other agents.

Structural examples of BDNF include, without limitation, full-length BDNF polypeptide, a functional fragment of BDNF polypeptide, an analog of BDNF polypeptide, a derivative of BDNF polypeptide, full-length BDNF RNA, a functional fragment of BDNF RNA, an analog of BDNF RNA, a derivative of BDNF RNA, a vector encoding full-length BDNF polypeptide, a vector encoding a functional fragment of BDNF polypeptide, a vector encoding an analog of BDNF polypeptide, a vector encoding a derivative of BDNF polypeptide.

Any agent that mimics, activates, stimulates, potentiates or increases the biological activity of TrkB can be used as a TrkB agonist. TrkB agonists include purified or recombinant nucleic acids that encode TrkB proteins or fragments thereof, purified or recombinant TrkB polypeptides or fragments thereof, or other agents that mimic, activate, stimulate, potentiate or increase the biological activity of TrkB.

Functional examples of TrkB agonists include, without limitation, agents that increase TrkB mRNA or protein, agents that increase TrkB signaling activity, agents that enhance BDNF mRNA or protein expression, agents that increase interaction between TrkB and its ligand BDNF (e.g., bivalent antibodies that bind TrkB and BDNF, fusion proteins with CDR combinations that bind TrkB and BDNF), and other agents.

Structural examples of a TrkB agonist include, without limitation, a small molecule such as N,N',N"-tris(2-hydroxyethyl)-1,3,5-benzenetricarboxamide (LM22A-4) (Massa S M, et al. J Clin Invest. 2010; 120:1774-85), a functional fragment of LM22A-4, an analog of LM22A-4, a derivative of LM22A-4, a peptide, an antibody, an antibody fragment, an inhibitor of GRK2, wherein the inhibitor of GRK2 is a small molecule, a peptide, an antibody, an antibody fragment, a vector encoding a dominant negative isoform of GRK2, or a vector encoding an antisense nucleic acid molecule targeting GRK2. A vector encoding TrkB, or a functional fragment thereof, may also be referred to as a TrkB agonist.

Any agent that opposes, deactivates, de-stimulates, de-potentiates or decreases the biological activity of βAR can be used as a βAR-blocker. βAR-blockers include purified or recombinant nucleic acids that encode βAR-blockers or fragments thereof, purified or recombinant βAR-blocker polypeptides or fragments thereof, or other agents that oppose, deactivate, de-stimulate, de-potentiate or decrease the biological activity of βAR.

Functional examples of βAR-blockers include, without limitation, agents that decrease βAR mRNA or protein, agents that decrease βAR signaling activity, agents that decrease cardiac responsiveness to catecholamines, and other agents.

Structural examples of βAR-blockers include, without limitation, Bisoprolol, Carvedilol, Carvedilol phosphate, Metoprolol Succinate, and Nebivolol, a functional fragment of any one or more of Bisoprolol, Carvedilol, Carvedilol phosphate, Metoprolol Succinate, and Nebivolol, an analog of any one or more of Bisoprolol, Carvedilol, Carvedilol phosphate, Metoprolol Succinate, and Nebivolol, and a derivative of any one or more of Bisoprolol, Carvedilol, Carvedilol phosphate, Metoprolol Succinate, and Nebivolol.

In various embodiments, the invention provides a composition for agonizing the biological function of TrkB, comprising the use of an agent that promotes the interaction between TrkB and BDNF. In various embodiments, the agent is BDNF or a fragment of BDNF. In various embodiments, the agent is an agent that binds to TrkB. In various embodiments, the agent is a small molecule, such as a small molecule mimic of BDNF. In various embodiments, the agent is N,N',N"-tris(2-hydroxyethyl)-1,3,5-benzenetricarboxamide (LM22A-4) (Massa S M, et al. J Clin Invest. 2010; 120:1774-85). In various embodiments, the agent is 7,8-dihydroxyflavone (Jang, S W et al., 2010, PNAS, 107 (6):2687-2692). In various embodiments, the agent is an antibody or an antibody fragment that mimics the biological function of BDNF. In various embodiments, the invention provides a composition for antagonizing the biological function of βAR, comprising the use of an agent that decreases the interaction between βAR and catecholamines.

In various embodiments, a therapeutic agent for treatment of diseases associated with BDNF and/or TrkB agonists and associated molecules and pathways thereof, modulates the expression, activity or amount of BDNF and/or TrkB agonists in a cell.

Nucleic Acids

In one embodiment, the invention provides a composition comprising BDNF, a TrkB agonist, βAR-blocker, or a combination thereof. In one embodiment, the invention provides a composition comprising regulators of BDNF, a TrkB agonist, βAR-blocker, or a combination thereof. In various embodiments, compositions comprise nucleic acid sequences, including without limitation, cDNA, sense and/or antisense sequences.

In various embodiments, a composition comprises an expression vector having an isolated nucleic acid or cDNA sequence or synthetic nucleic acid sequence, encoding the desired molecules, or regulators thereof. The term "nucleic acid sequence" will be used for the sake of brevity and will include, without limitation, isolated nucleic acid or cDNA sequences, synthesized or synthetic nucleic acid sequences, chimeric nucleic acid sequences, homologs, orthologs, variants, mutants or combinations thereof.

In various embodiments, a nucleic acid sequence of BDNF comprises at least about a 50% sequence identity to wild type BDNF and/or TrkB agonist or cDNA sequences thereof. In other embodiments, the BDNF and/or TrkB agonist nucleic acid sequence comprises at least about 75%, 80%, 85%, 90%, 95%, 96%, 97%, 98%, 99% sequence identity to wild type BDNF and/or TrkB agonist or cDNA sequences thereof.

In various embodiments, a nucleic acid sequence of BDNF and/or TrkB agonist further comprises one or more mutations, substitutions, deletions, variants or combinations thereof.

In various embodiments, a nucleic acid sequence of an activator of BDNF and/or an activator of TrkB signaling comprises at least about a 50% sequence identity to wild type activator of BDNF and/or an activator of TrkB signaling. In other embodiments, the activator of BDNF and/or activator of TrkB signaling nucleic acid sequence comprises at least about 75%, 80%, 85%, 90%, 95%, 96%, 97%, 98%, 99% sequence identity to wild type activator of BDNF and/or an activator of TrkB signaling or cDNA sequences thereof.

In various embodiments, a nucleic acid sequence of an activator of BDNF and/or an activator of TrkB signaling further comprises one or more mutations, substitutions, deletions, variants or combinations thereof.

In various embodiments, a nucleic acid sequence of an inhibitor of an antagonist of BDNF and/or TrkB signaling is provided. In one embodiment, the antagonist of BDNF and/or TrkB signaling is GRK2. In one embodiment, the inhibitor of GRK2 is an antisense nucleic acid targeting GRK2.

In various embodiments, a nucleic acid sequence of an inhibitor of an antagonist of BDNF and/or TrkB signaling comprises at least about a 50% sequence identity to a reference inhibitor of an antagonist of BDNF and/or TrkB signaling. In other embodiments, the inhibitor of an antagonist of BDNF and/or TrkB signaling nucleic acid sequence comprises at least about 75%, 80%, 85%, 90%, 95%, 96%, 97%, 98%, 99% sequence identity to a reference inhibitor of an antagonist of BDNF and/or TrkB signaling or sequences thereof.

In various embodiments, a nucleic acid sequence of an inhibitor of an antagonist of BDNF and/or TrkB signaling further comprises one or more mutations, substitutions, deletions, variants or combinations thereof.

In some embodiments, the homology, sequence identity or complementarity, between a BDNF and/or TrkB agonist nucleic acid sequence comprising one or more mutations, substitutions, deletions, variants or combinations thereof and the native or wild type or cDNA sequences of BDNF and/or TrkB agonist is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, the homology, sequence identity or complementarity, between an activator of BDNF and/or an activator of TrkB signaling nucleic acid sequence comprising one or more mutations, substitutions, deletions, variants or combinations thereof and the native or wild type or cDNA sequences of an activator of BDNF and/or an activator of TrkB signaling is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, the homology, sequence identity or complementarity, between an inhibitor of an antagonist of BDNF and/or TrkB signaling nucleic acid sequence comprising one or more mutations, substitutions, deletions, variants or combinations thereof and the native or reference sequences of an inhibitor of an antagonist of BDNF and/or TrkB signaling is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

Vectors

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31-40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2.mu. plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

A number of vectors are known to be capable of mediating transfer of gene products to mammalian cells, as is known in the art and described herein. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). A large variety of such vectors are known in the art and are generally available.

Suitable nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide e.g., a cytomegalovirus (CMV) promoter.

Additionally, preferred vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector (Geller, A. I. et al., J. Neurochem, 64: 487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A.: 90 7603 (1993); Geller, A. I., et al., Proc Natl. Acad. Sci USA: 87:1149 (1990)), Adenovirus Vectors (LeGal LaSalle et al., Science, 259:988 (1993); Davidson, et al., Nat. Genet. 3: 219 (1993); Yang, et al., J. Virol. 69: 2004 (1995)) and Adeno-associated Virus Vectors (Kaplitt, M. G., et al., Nat. Genet. 8:148 (1994)).

Pox viral vectors introduce the gene into the cell's cytoplasm. Avipox virus vectors result in only a short-term expression of the nucleic acid. Adenovirus vectors, adeno-associated virus vectors and herpes simplex virus (HSV) vectors may be an indication for some invention embodiments. The adenovirus vector results in a shorter-term expression (e.g., less than about a month) than adeno-associated virus (AAV), in some embodiments, may exhibit much longer expression. In some embodiments, the expression vector is an AAV9 vector. The particular vector chosen will depend upon the target cell and the condition being treated. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., Hum Gene Ther 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an E. coli origin of replication. See Sambrook, et al., Molecular Cloning: A Laboratory Manual, Cold Spring Harbor Laboratory press, (1989). The plasmid vector may also include a selectable marker such as the beta-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, BioTechniques, 6:682 (1988). See also, Felgner and Holm, Bethesda Res. Lab. Focus, 11(2):21 (1989) and Maurer, R. A., Bethesda Res. Lab. Focus, 11(2):25 (1989).

Replication-defective recombinant adenoviral vectors, can be produced in accordance with known techniques. See Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the molecules of the invention intracellularly, for example, cardiac tissues. See for example, Chen et al, BioTechniques, 34: 167-171 (2003), which is incorporated herein, by reference, in its entirety.

Expression of the molecules of the invention may be controlled by any promoter/enhancer element known in the art, but these regulatory elements must be functional in the host selected for expression. In some embodiments, the promoter is a tissue specific promoter. Of particular interest are muscle specific promoters, and more particularly, cardiac specific promoters. These include the myosin light chain-2 promoter (Franz et al. (1994) Cardioscience, Vol. 5(4):235-43; Kelly et al. (1995) J. Cell Biol., Vol. 129(2):383-396), the alpha actin promoter (Moss et al. (1996) Biol. Chem., Vol. 271(49):31688-31694), the troponin 1 promoter (Bhaysar et al. (1996) Genomics, Vol. 35(1):11-23); the $Na^+/Ca^{2+}$ exchanger promoter (Barnes et al. (1997) J. Biol. Chem., Vol. 272(17):11510-11517), the dystrophin promoter (Kimura et al. (1997) Dev. Growth Differ., Vol. 39(3):257-265), the alpha7 integrin promoter (Ziober and Kramer (1996) J. Bio. Chem., Vol. 271(37):22915-22), the brain natriuretic peptide promoter (LaPointe et al. (1996) Hypertension, Vol. 27(3 Pt 2):715-22) and the alpha B-crystallin/small heat shock protein promoter (Gopal-Srivastava (1995) J. Mol. Cell. Biol., Vol. 15(12):7081-7090), alpha myosin heavy chain promoter (Yamauchi-Takihara et al. (1989) Proc. Natl. Acad. Sci. USA, Vol. 86(10):3504-3508) and the ANF promoter (LaPointe et al. (1988) J. Biol. Chem., Vol. 263(19):9075-9078).

Other promoters which may be used to control expression of the molecules of the invention include, but are not limited to, cytomegalovirus (CMV) promoter (U.S. Pat. Nos. 5,385, 839 and 5,168,062), the SV40 early promoter region (Benoist and Chambon, 1981, Nature 290:304-310), the promoter contained in the 3' long terminal repeat of Rous sarcoma virus (Yamamoto, et al., Cell 22:787-797, 1980), the herpes thymidine kinase promoter (Wagner et al., Proc. Natl. Acad. Sci. U.S.A. 78:1441-1445, 1981), the regulatory sequences of the metallothionein gene (Brinster et al., Nature 296:39-42, 1982); prokaryotic expression vectors such as the β-lactamase promoter (Villa-Kamaroff, et al., Proc. Natl. Acad. Sci. U.S.A. 75:3727-3731, 1978), or the tac promoter (DeBoer, et al., Proc. Natl. Acad. Sci. U.S.A. 80:21-25, 1983); see also "Useful proteins from recombinant bacteria" in Scientific American, 242:74-94, 1980; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., Cell 38:639-646, 1984; Ornitz et al., Cold Spring Harbor Symp. Quant. Biol. 50:399-409, 1986; MacDonald, Hepatology 7:425-515, 1987); insulin gene control region which is active in pancreatic beta cells (Hanahan, Nature 315:115-122, 1985), immunoglobulin gene control region which is active in lymphoid cells (Grosschedl et al., Cell 38:647-658, 1984; Adames et al., Nature 318:533-538, 1985; Alexander et al., Mol. Cell. Biol. 7:1436-1444, 1987), mouse mammary tumor virus control region which is active in testicular, breast, lymphoid and mast cells (Leder et al., Cell 45:485-495, 1986), albumin gene control region which is active in liver (Pinkert et al., Genes and Devel. 1:268-276, 1987), alpha-fetoprotein gene control region which is active in liver (Krumlauf et al., Mol. Cell. Biol. 5:1639-1648, 1985; Hammer et al., Science 235:53-58, 1987), alpha 1-antitrypsin gene control region which is active in the liver (Kelsey et al., Genes and Devel. 1: 161-171, 1987), beta-globin gene control region which is active in myeloid cells (Mogram et al., Nature 315:338-340, 1985; Kollias et al., Cell 46:89-94, 1986), myelin basic protein gene control region which is active in oligodendrocyte cells in the brain (Readhead et al., Cell 48:703-712, 1987), myosin light chain-2 gene control region which is active in skeletal muscle (Sani, Nature 314:283-286, 1985), and gonadotropic releasing hormone gene control region which is active in the hypothalamus (Mason et al., Science 234:1372-1378, 1986).

Yeast expression systems can also be used according to the invention to express the molecules of the invention. For example, the non-fusion pYES2 vector (XbaI, SphI, ShoI, NotI, GstXI, EcoRI, BstXI, BamH1, SacI, KpnI, and HindIII cloning sites; Invitrogen) or the fusion pYESHisA, B, C (XbaI, SphI, ShoI, NotI, BstXI, EcoRI, BamH1, SacI, KpnI, and HindIII cloning sites, N-terminal peptide purified with ProBond resin and cleaved with enterokinase; Invitrogen), to mention just two, can be employed according to the invention. A yeast two-hybrid expression system can be prepared in accordance with the invention.

One preferred delivery system is a recombinant viral vector that incorporates one or more of the polynucleotides therein, preferably about one polynucleotide. Preferably, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

In some embodiments, the vector is an adenovirus-associated viral vector (AAV), for example, AAV9. The term "AAV vector" means a vector derived from an adeno-associated virus serotype, including without limitation, AAV-1, AAV-2, AAV-3, AAV-4, AAV-5, AAV-6, AAV-7 and AAV-8. AAV vectors can have one or more of the AAV wild-type genes deleted in whole or part, preferably the rep and/or cap genes, but retain functional flanking ITR sequences. Despite the high degree of homology, the different serotypes have tropisms for different tissues. The receptor for AAV1 is unknown; however, AAV1 is known to transduce skeletal and cardiac muscle more efficiently than AAV2. Since most of the studies have been done with pseudotyped vectors in which the vector DNA flanked with AAV2 ITR is packaged into capsids of alternate serotypes, it is clear that the biological differences are related to the capsid rather than to the genomes. Recent evidence indicates that DNA expression cassettes packaged in AAV 1 capsids are at least 1 log 10 more efficient at transducing cardiomyocytes than those packaged in AAV2 capsids. In one embodiment, the viral delivery system is an adeno-associated viral delivery system. The adeno-associated virus can be of serotype 1 (AAV 1), serotype 2 (AAV2), serotype 3 (AAV3), serotype 4 (AAV4), serotype 5 (AAV5), serotype 6 (AAV6), serotype 7 (AAV7), serotype 8 (AAV8), or serotype 9 (AAV9).

Some skilled in the art have circumvented some of the limitations of adenovirus-based vectors by using adenovirus "hybrid" viruses, which incorporate desirable features from adenovirus as well as from other types of viruses as a means of generating unique vectors with highly specialized properties. For example, viral vector chimeras were generated between adenovirus and adeno-associated virus (AAV). These aspects of the invention do not deviate from the scope of the invention described herein.

Nucleic acids encoding the molecules of the invention may be delivered to cardiac muscle by methods known in the art (see e.g., US Patent Appln. Publication No. US 2009/0209631). For example, cardiac cells of a large mammal may be transfected by a method that includes dilating a blood vessel of the coronary circulation by administering a vasodilating substance to the mammal prior to, and/or concurrent with, administering the nucleic acids. In some embodiments, the method includes administering the nucleic acids into a blood vessel of the coronary circulation in vivo, wherein nucleic acids are infused into the blood vessel over a period of at least about three minutes, wherein the coronary circulation is not isolated or substantially isolated from the systemic circulation of the mammal, and wherein the nucleic acids transfect cardiac cells of the mammal.

In some embodiments, the subject can be a human, an experimental animal, e.g., a rat or a mouse, a domestic animal, e.g., a dog, cow, sheep, pig or horse, or a non-human primate, e.g., a monkey. The subject may be suffering from a cardiac disorder, such as heart failure, ischemia, myocardial infarction, congestive heart failure, arrhythmia, transplant rejection and the like. In a preferred embodiment, the subject is suffering from heart failure. In another particular embodiment, the subject is suffering from arrhythmia. In one embodiment, the subject is a human. For example, the subject is between ages 18 and 65. In another embodiment, the subject is a non-human animal.

In one embodiment, the subject has or is at risk for heart failure, e.g. a non-ischemic cardiomyopathy, mitral valve regurgitation, ischemic cardiomyopathy, or aortic stenosis or regurgitation.

In some embodiments, transfection of cardiac cells with nucleic acids encoding the molecules of the invention fused to an effector domain increases lateral ventricle fractional shortening. In some embodiments, the mammal is human and the disease is congestive heart failure. In some embodiments, the transfection of the cardiac cells increases lateral ventricle fractional shortening when measured about 4 months after the infusion by at least 25% as compared to lateral ventricle fractional shortening before infusion of the polynucleotide. In some embodiments, the transfection of the cardiac cells results in an improvement in a measure of cardiac function, such as expression of BDNF and/or TrkB protein, fractional shortening, ejection fraction, cardiac output, time constant of ventricular relaxation, and regurgitant volume.

A treatment can be evaluated by assessing the effect of the treatment on a parameter related to contractility. For example, SR $Ca^{2+}$ ATPase activity or intracellular $Ca^{2+}$ concentration can be measured. Furthermore, force generation by hearts or heart tissue can be measured using methods described in Strauss et al., Am. J. Physiol., 262:1437-45, 1992, the contents of which are incorporated herein by reference.

Modified Nucleic Acids

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produced in high yield via in vitro transcription using plasmids such as pGEM® T vector or SP65 (Promega Corporation, Madison, Wis.).

Accordingly, certain preferred nucleic acid sequences of this invention are chimeric nucleic acid sequences. "Chimeric nucleic acid sequences" or "chimeras," in the context of this invention, contain two or more chemically distinct regions, each made up of at least one nucleotide. These sequences typically contain at least one region of modified nucleotides that confers one or more beneficial properties (such as, for example, increased nuclease resistance, increased uptake into cells, increased binding affinity for the target).

Chimeric nucleic acid sequences of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

Specific examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Examples of oligonucleotides with phosphorothioate backbones and those with heteroatom backbones, include without limitation: $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH). The amide backbones disclosed by De Mesmaeker et al. (1995) Acc. Chem. Res. 28:366-374 are also one example. In other embodiments, a nucleic acid sequence comprises morpholino backbone structures (Summerton and Weller, U.S. Pat. No. 5,034,506). In other embodiments, such as the peptide nucleic acid (PNA) backbone, the phosphodiester backbone of the nucleic acid sequence is replaced with a polyamide backbone, the nucleotides being bound directly or indirectly to the aza nitrogen atoms of the polyamide backbone (Nielsen et al. (1991) Science 254, 1497). Nucleic acid sequences may also comprise one or more substituted sugar moieties. Examples include: OH, SH, $SCH_3$, F, OCN, $OCH_3$ $OCH_3$, $OCH3O(CH_2)_nCH_3$, $O(CH_2)_n$ $NH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a reporter group; an intercalator; a group for improving the pharmacokinetic properties of an oligonucleotide; or a group for improving the pharmacodynamic properties of an oligonucleotide and other substituents having similar properties. Other modifications include, for example: 2'-methoxyethoxy [2'-O—$CH_2CH_2OCH_3$, also known as 2'-O-(2-methoxyethyl)] (Martin et al., (1995) Hely. Chim. Acta, 78, 486), 2'-methoxy (2'-O—$CH_3$), 2'-propoxy (2'-$OCH_2CH_2CH_3$) and 2'-fluoro (2'-F). Similar modifications may also be made at any positions on the oligonucleotide, the 2' or the 3' position of the sugar on the 3' terminal nucleotide and the 5' position of 5' terminal nucleotide. The nucleic acid sequences may also have sugar mimetics such as cyclobutyls in place of the pentofuranosyl group.

Preferred modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

The nucleic acid sequences may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W.H. Freeman & Co., San Francisco, 1980, pp 75-77; Gebeyehu, G., (1987) et al. Nucl. Acids Res. 15:4513). A "universal" base known in the art, e.g., inosine, may be included.

Another modification involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, cholic acid, a thioether, e.g., hexyl-5-tritylthiol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Nucleic acid sequences comprising lipophilic moieties, and methods for preparing such oligonucleotides are known in the art, for example, U.S. Pat. Nos. 5,138,045, 5,218,105 and 5,459,255.

It is not necessary for all positions in a given nucleic acid sequence to be uniformly modified, and in fact more than one of the aforementioned modifications may be incorporated in a single nucleic acid sequence or even at within a single nucleoside within a such sequence. The present invention also includes oligonucleotides which are chimeric oligonucleotides as hereinbefore defined.

In another embodiment, the molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

In another embodiment, the nucleic acid sequences comprise one or more nucleotides substituted with locked nucleic acids (LNA). The LNA modified nucleic acid sequences may have a size similar to the parent or native sequence or may be larger or preferably smaller. It is preferred that such LNA-modified oligonucleotides contain less than about 70%, more preferably less than about 60%, most preferably less than about 50% LNA monomers and that their sizes are between about 1 and 25 nucleotides.

Antisense Oligonucleotides

In one embodiment, an oligonucleotide comprises at least five consecutive bases complementary to a nucleic acid sequence, wherein the oligonucleotide specifically hybridizes to and modulates expression of a desired target (e.g. in vivo or in vitro). In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligonucleotide. These compounds are then tested to determine their ability to inhibit expression of a target nucleic acid.

In some embodiments, homology, sequence identity or complementarity, between the oligonucleotide and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, an oligonucleotide comprises combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another preferred embodiment, an oligonucleotide optionally comprises at least one modified nucleobase comprising, peptide nucleic acids, locked nucleic acid (LNA) molecules, analogues, derivatives and/or combinations thereof.

An oligonucleotide is specifically hybridizable when binding of the compound to the target nucleic acid interferes with the normal function of the target nucleic acid to cause a loss of activity, and there is a sufficient degree of complementarity to avoid non-specific binding of the oligonucleotide to non-target nucleic acid sequences under conditions in which specific binding is desired. Such conditions include, i.e., physiological conditions in the case of in vivo assays or therapeutic treatment, and conditions in which assays are performed in the case of in vitro assays.

An oligonucleotide, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the oligonucleotide to non-target sequences under conditions in which specific binding is desired, i.e., under physiological conditions in the case of in vivo assays or therapeutic treatment, and in the case of in vitro assays, under conditions in which the assays are performed.

The specificity and sensitivity of antisense is also harnessed by those of skill in the art for therapeutic uses. Antisense oligonucleotides have been employed as therapeutic moieties in the treatment of disease states in animals and humans. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric oligonucleotides, particularly oligonucleotides, bind to target nucleic acid molecules and modulate the expression of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The oligonucleotides include antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an oligonucleotide to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule. An example of a "function" can be one which inhibits a negative regulator of transcription, thus allowing for an increased expression of a desired molecule, such as, for example, BDNF and/or a BDNF agonist.

In another preferred embodiment, the antisense oligonucleotides bind to sense polynucleotides and modulate the expression and/or function of the target molecule.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non-coding regions.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs).

Small double-stranded RNA (dsRNA) may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In some embodiments, the ribonucleic acid sequence is specific for regulatory segments of the genome that control the transcription of BDNF and/or a TrkB agonist, or a regulator thereof. Thus a candidate therapeutic agent can be a dsRNA that activates the expression of BDNF and/or a TrkB agonist, or deactivates a negative regulator of BDNF and/or a TrkB agonist, in a cell and is administered to a patient in need of treatment.

Peptides

In another embodiment, a BDNF and/or a TrkB agonist peptide is encoded by a nucleic acid comprising a BDNF and/or a TrkB agonist wild type, chimeric or cDNA sequences thereof. The peptide can also be a synthetic peptide of BDNF and/or a TrkB agonist.

In another embodiment, a regulator of BDNF and/or a TrkB agonist is encoded by a nucleic acid comprising regulator wild type, chimeric or cDNA sequences thereof. The peptide can also be a synthetic peptide of a regulator of BDNF and/or a TrkB agonist.

It is to be understood that the peptide sequences are not limited to the native or cDNA sequences thereof. The skilled artisan will recognize that conservative amino acid changes may be made, which although they alter the primary sequence of the protein or peptide, do not normally alter its function. Conservative amino acid substitutions typically include substitutions within the following groups: glycine, alanine, valine, isoleucine, leucine; aspartic acid, glutamic acid, asparagine, glutamine, serine, threonine, lysine, arginine, phenylalanine, tyrosine.

Conservative substitutions may also be made based on types of amino acids: aliphatic (valine, isoleucine, leucine, and alanine); charged (aspartic acid, glutamic acid, lysine, arginine, and histidine); aromatic residues (phenylalanine, tyrosine and tryptophan); and sulfur-containing (methionine and cysteine). Polypeptide sequences having at least about 68% identity, at least about 70% identity, or at least about 71% identity to a reference nucleic acid sequence, or cDNA sequences thereof are contemplated by the present invention.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator blast.ncbi.nlm.nih.gov/Blast.cgi. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used. In calculating percent identity, exact matches are typically counted.

Embodiments of the invention also include polynucleotides encoding hybrid proteins comprising BDNF and/or TrkB agonist polypeptide, or polypeptides of regulators thereof, operatively fused directly or indirectly via peptide linker, to a second polypeptide sequence. Linker sequences are well known in the art. In one embodiment, a hybrid protein comprises a BDNF and/or TrkB agonist polypeptide or a BDNF and/or TrkB agonist polypeptide operatively fused to a detectable moiety, such as, a reporter polypeptide, wherein the reporter polypeptide is fused to the N- or C-terminal of the BDNF and/or TrkB agonist polypeptide, directly or indirectly. Exemplary reporter polypeptides include luciferase (LUC), green fluorescent protein (GFP), and GFP derivatives.

Hybrid proteins comprising a BDNF and/or TrkB agonist polypeptide, or a polypeptide regulator thereof, or fragment thereof may be linked to other types of polypeptides, in addition to a reporter polypeptide, or in lieu of a reporter polypeptide. These additional polypeptides may be any amino acid sequence useful for the purification, identification, and/or therapeutic or prophylactic application of the peptide. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Anti-TrkB Activating Antibodies

Another aspect of the present invention involves activating anti-TrkB antibodies. An activating antibody differs from an inhibiting antibody because it amplifies or substitutes for the effects of BDNF on TrkB. In one embodiment, the activating antibody is able to bind to TrkB and cause it to be activated in the absence of BDNF. This type of activating antibody is essentially a mimic of BDNF. In another embodiment, the activating antibody amplifies the effect of BDNF on TrkB. This type of antibody does not activate TrkB by itself, but rather increases the activation of TrkB in the presence of BDNF. A mimic anti-TrkB antibody may be easily distinguished from an amplifying anti-TrkB antibody by treating cells in vitro with an antibody in the presence or absence of low levels of BDNF. If the antibody is able to cause TrkB activation in the absence of BDNF, e.g., it increases TrkB activity, then the antibody is a mimic antibody. If the antibody cannot cause TrkB activation in the absence of BDNF but is able to amplify the amount of TrkB activation, then the antibody is an amplifying antibody.

Dominant Negative GRK2 Isoforms

Another aspect of the present invention involves dominant negative isoforms of GRK2. The dominant negative isoforms may be in any of the structural forms contemplated by the present invention, including but not limited to a polypeptide or fragment thereof, and a nucleic acid encoding a polypeptide or fragment thereof. In various embodiments, the dominant negative isoform of GRK2 lacks kinase activity. In various embodiments, the dominant negative isoform lacks target binding activity. In various embodiments, the dominant negative isoform interferes with the function or activity of wild-type GRK2.

βAR-Blockers

The compositions of the present invention may comprise a β-adrenoceptor blocker, a pharmaceutically acceptable derivate or salt thereof, or mixtures thereof.

The term "β-adrenoceptor blocker" or "βAR-blocker" as used herein refers to beta-adreno receptor blockers ("beta blockers"), which competitively and reversibly bind to β-adrenergic receptors. When bound to the β-adrenergic receptors, the βAR-blockers prevent the adrenergic stimulation through endogenous catecholamines (epinephrine (adrenaline) and norepinephrine (noradrenaline)) in particular.

In one embodiment, the βAR-blocker binds to $\beta_1AR$, $\beta_2AR$, $\beta_3AR$ or any combination thereof. In one embodiment, the βAR-blocker is selective for $\beta_1AR$. In one embodiment, the βAR-blocker is selective for $\beta_2AR$. In one embodiment, the βAR-blocker is selective for $\beta_3AR$.

The βAR-blockers are negative inotrops (reduce myocardial contractility), negative chronotrops (reduce heart rate), negative dromotrops (reduce atrial-ventricular conduction rate), and positive lusitrops (support relaxation of the myocard). By this action βAR-blockers suspend the circulus virtuosus derived from constantly elevated deleterious endogenous catecholamine levels, which mediate a constant "fight or flight" response.

Suitable βAR-adrenoceptor blockers include, without limitation, propanolol, metoprolol, atenolol, bisoprolol, pindolol, alprenolol, carvedilol, acebutolol, betaxolol, esmolol, nebivolol, CGP 20712, SR 59230A, CGP-12177, ICI 118551, pharmaceutically acceptable salts, derivates, metabolites, pro-drugs, and combinations thereof. In one embodiment, the βAR-blocker may be bisoprolol, a pharmaceutically acceptable salt, derivate, metabolite, pro-drug, or combinations thereof. In another embodiment, the βAR-blocker may be bisoprolol fumarate.

Bisoprolol fumarate may be purchased commercially from Merck KgA, Darmstadt, Germany (EMD Pharmaceuticals in the US) or made in accordance with methods generally known in the art.

The βAR-blocker may be administered by itself or it may also be administered as part of a formulation. The formulation may be a solid, gas, or liquid formulation. In one embodiment, the formulation is a liquid formulation. In another embodiment, the liquid formulation may include from about 0.001% to about 10% by weight βAR-blockers, from about 40% to about 80% by weight of a solvent, such as water, and from about 1% to about 70% by weight of a thickener, such as glycerine or hydroxypropyl methylcellulose. The formulation may also include other ingredients such as preservatives, solvents, and flavorings, among others. In another embodiment, the formulation may be, for example, as detailed in PCT Publication WO 2007/124869, which is hereby incorporated by reference in its entirety. In yet another embodiment, the formulation may include from about 0.01 to about 1% by weight bisoprolol fumarate.

In one embodiment, the βAR-blockers are administered once a day. In another embodiment, the βAR-blockers are administered multiple times a day. In yet another embodiment, the βAR-blockers are administered at a dose of from about 0.001 mg/kg to about 100 mg/kg. In a further embodiment, the βAR-blockers are administered at a dose of from about 0.001 mg/kg to about 10 mg/kg. In another embodiment, the βAR-blockers are administered at a dose of from about 0.001 mg/kg to about 1 mg/kg.

The βAR-blockers may be administered in the form of, for example, tablets, capsules, solutions, gel capsules, pastes. In one embodiment, the βAR-blockers may be administered in the form of an oral solution. Alternatively, the βAR-blockers may be administered by parenteral administration, such as, for example, by injection (intramuscular, subcutaneous, intravenous, intraperitoneal and the like), implants, or by nasal administration.

The βAR-blockers may be administered once or in multiple doses. Alternatively, the βAR-blockers may be administered continuously as necessary throughout the day.

Humans having heart disease may be treated by at least one βAR-blocker of the present invention. Animals having heart disease who may be treated include farm animals, such as cattle, horses, sheep, pigs, goats, camels, water buffalo, donkeys, rabbits, fallow deer, reindeer, furbearing animals such as mink, chinchilla, raccoons, birds, such as chickens, geese, turkeys, ducks, pigeons, species of birds intended to be kept in the home and in zoos, and fish. Other animals include laboratory and experimental animals, such as mice, rats, guinea pigs, hamsters, dogs, cats, and MUMS (minor use and minor species). Yet other animals include pets and hobby animals, such as rabbits, hamsters, guinea pigs, mice, horses, reptiles, corresponding species of birds, dogs, and cats.

Methods

In one embodiment, the invention provides a method for treating a cardiovascular disease or disorder in a subject comprising administering a composition which directly or indirectly modulates the amount or activity of BDNF, TrkB, βAR, or a combination thereof.

In one embodiment, the invention provides a method for treating a cardiovascular disease or disorder in a subject comprising administering a composition which directly or indirectly agonizes TrkB signaling and directly or indirectly antagonizes βAR signaling.

In one embodiment, the invention provides a method for treating a cardiovascular disease or disorder in a subject comprising administering a composition comprising BDNF, a TrkB agonist, βAR-blocker, or a combination thereof to a subject in need thereof.

In one embodiment, the present invention provides the use of BDNF, a TrkB agonist, βAR-blocker, or a combination thereof for the preparation of a pharmaceutical composition for the treatment or prevention of a cardiac or cardiovascular disease in a patient in need thereof. In some instances, by a cardiac or cardiovascular disease is meant a stage of disease characterized by prior to the onset, the onset, or the progression of HF, and may be before or after a stroke or myocardial infarct.

In one embodiment the cardiac or cardiovascular disease is at least one of left ventricular hypertrophy, coronary artery disease, essential hypertension, acute hypertensive emergency, cardiomyopathy, heart insufficiency, exercise intolerance, chronic heart failure, arrhythmia, cardiac dysrhythmia, syncopy, atherosclerosis, mild chronic heart failure, angina pectoris, cardiac bypass reocclusion, intermittent claudication (atheroschlerosis oblitterens), diastolic dysfunction and systolic dysfunction.

The methods and compositions of the present invention may be used to treat advanced class 3B and class 4 heart failure, acute decompensated heart failure, cardio renal syndrome defined by biventricular failure, decreased glomerular filtration rate and systemic congestion, as well as acute coronary syndromes and microvascular angina. These compositions and methods have the possibility to reduce symptoms, reduce hospitalizations and increase the quality of life for patients with these conditions. In preferred embodiments the compositions are administered by continuous intravenous infusion which may be combined with standard therapies.

In another embodiment the patient suffers from a disease such as myocardial infarct, acute coronary syndrome, unstable angina, non-Q-wave cardiac necrosis, Q-wave myocardial infarct or morbidity after stroke.

In another embodiment, the patient having the cardiovascular disease is a diabetic patient. In yet another embodiment, the patient having the cardiovascular disease is a non-diabetic patient.

The methods and compositions of the present invention may be used to provide acute cardioprotective effects, such as reducing the incidence of sudden death due to arrhythmias or contractile failure in a subject with an acute occlusion of a coronary artery (myocardial infarction); reducing damage occurring during reperfusion of the heart muscle after ischemia ('hypoxia-reperfusion injury' or 'ischemia-reperfusion injury'); reducing the amount of cardiac muscle that is damaged or reducing the severity of damage to the heart muscle caused by an acute coronary artery occlusion (often referred to as 'reducing infarct size'). Chronic cardioprotective effects include, but are not limited to, reducing pathologic remodeling of the cardiac chambers, including chamber dilation, consequent to an acute coronary artery occlusion; reducing apoptosis in cardiac muscle consequent to an acute coronary artery occlusion; reducing the impairment of contractility of cardiac muscle consequent to an acute coronary occlusion; and reducing long-term mortality in subjects have suffered damage to the heart muscle caused by an acute coronary occlusion.

Acute and/or chronic cardioprotective effects can be desirable in subjects with chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have an inotropic effect, increasing the strength of contraction in a failing heart. Acute and chronic inotropic effects may be desirable in acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention may also have an anti-arrhythmic effect. This effect can be acute or chronic, and can include effects that are attributable to prevention and/or reduction of injury to the heart muscle. Examples of anti-arrhythmic effects include, but are not limited to, reducing the incidence and altering the rates of cardiac arrhythmias (including but not limited to atrial fibrillation, other supraventricular arrhythmias, ventricular tachycardia and ventricular fibrillation) following coronary occlusion.

The methods and compositions of the present invention may also have an anti-hypertrophic effect. Anti-hypertrophic effects can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have lusitropic effects, improving the relaxation of the heart muscle during diastole. Lusitropic effects can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have anti-arrhythmic effects of benefit in the treatment of disorders of the heart rhythm, examples of which include but are not limited to atrial fibrillation, ventricular tachycardia and ventricular fibrillation. These effects, which can include reductions in the incidence and rate of the arrhythmias, can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The patient treated using the methods and compositions of the present invention can also be at an increased risk of developing heart disease. This can include (but is not limited to) individuals with hypertension (systemic or pulmonary), obesity, endocrine disease (including diabetes, thyroid disease, adrenal disease, dysregulation of homocysteine metabolism), iron storage disease, amyolidosis, renal disease, connective tissue disease, infectious diseases, thromboembolic disease, immune diseases, hematologic diseases.

Provided herein are methods of increasing or enhancing the chances of survival of a subject with heart disease, comprising administering to a subject in need thereof an effective amount of BDNF, a TrkB agonist, βAR-blocker, or a combination thereof, or a regulator of BDNF, a TrkB agonist, βAR-blocker, or a combination thereof, thereby increasing or enhancing the chances of survival of the subject treated by a certain period of time, for example, by at least 10 days, 1 month, 3 months, 6 months, 1 year, 1.5 years, 2 years, 3 years, 4 years, 5 years, 8 years, or 10 years. The increase in survival of a subject can be defined, for example, as the increase in survival of a preclinical animal model by a certain period of time, for example, by at least 10 days, 1 month, 3 months, 6 months, or 1 year, or at least 2 times, 3 times, 4 times, 5 times, 8 times, or 10 times, more than a control animal model (that has the same type of disease) without the treatment with the inventive method. Optionally, the increase in survival of a mammal can also be defined, for example, as the increase in survival of a subject with heart disease by a certain period of time, for example, by at least 10 days, 1 month, 3 months, 6 months, 1 year, 1.5 years, 2 years, 3 years, 4 years, 5 years, 8 years, or 10 years more than a subject with the same type of heart disease but without the treatment with the inventive method. The control subject may be on a placebo or treated with supportive standard care such as chemical therapy, biologics and/or radiation that do not include the inventive method as a part of the therapy.

In various embodiments, the present invention includes methods for modulating the level or activity of BDNF in a subject, a cell, a tissue, or an organ in need thereof. In various embodiments, the methods of the invention increase the amount of BDNF polypeptide, the amount of BDNF mRNA, the amount of BDNF activity, or a combination thereof. In various embodiments, the present invention includes methods for modulating the level or activity of TrkB in a subject, a cell, a tissue, or an organ in need thereof. In various embodiments, the methods of the invention increase the amount of TrkB polypeptide, the amount of TrkB mRNA, the amount of TrkB activity, or a combination thereof. In various embodiments, the present invention includes methods for modulating the level or activity of TrkB agonist in a subject, a cell, a tissue, or an organ in need thereof. In various embodiments, the methods of the invention increase the amount of TrkB agonist polypeptide, the amount of TrkB agonist mRNA, the amount of TrkB agonist activity, or a combination thereof. In various embodiments, the present invention includes methods for modulating the level or activity of βAR in a subject, a cell, a tissue, or an organ in need thereof. In various embodiments, the methods of the invention decrease the amount of βAR polypeptide, the amount of βAR mRNA, the amount of βAR activity, or a combination thereof.

In various embodiments, the invention provides a method for agonizing the biological function of TrkB, comprising the administration of an agent that promotes the biological function of TrkB. In various embodiments, the agent is BDNF polypeptide or a fragment of BDNF polypeptide. In various embodiments, the agent is an agent that binds to TrkB. In various embodiments, the agent is a small molecule, such as a small molecule mimic of BDNF. In various embodiments, the agent is N,N',N''-tris(2-hydroxyethyl)-1, 3,5-benzenetricarboxamide (LM22A-4) (Massa S M, et al. J Clin Invest. 2010; 120:1774-85). In various embodiments, the agent is an antibody or antibody fragment that mimics the biological function of BDNF.

In various embodiments, the invention comprises a method of improving cardiac function in a subject with HF, by administering a composition comprising at least one of BDNF, a TrkB agonist and a βAR-blocker, or a regulator thereof. As used herein, "cardiac function" refers to a heart pumping blood at the level that would be expected of a healthy individual at a particular age. As would be understood by the skilled artisan, measurements for determining cardiac function may be acquired through any method known in the art. For example, the distance walked during a standardized 6-minute walk test is a good quantitative surrogate of exercise capacity (Brooks et al., Am J Respir Crit Care Med. 167:1287). In addition, gas analysis during a maximal effort supine-bicycle exercise test may provide parameters to determine peak oxygen consumption ($VO_2$) and exercise efficiency, as would be understood by one skilled in the art. As used herein, "exercise efficiency" refers to the external power output per amount of oxygen consumed.

In one embodiment, the invention comprises a method of increasing cardiac BDNF levels in a subject with HF, by administering a composition comprising at least one of BDNF, a TrkB agonist and a βAR-blocker, or a regulator thereof. As used herein, "cardiac BDNF levels" may be measured using serum BDNF levels as an approximation of cardiac BDNF levels. Methods of sampling serum and performing an assay to quantitate the amount of serum BDNF levels are known in the art. As a non-limiting example, the assay may be an immunoblot. In another non-limiting example, the assay may be chromatographic separation of serum components coupled with mass spectrometry.

In one embodiment, the invention comprises a method of decreasing cardiac fibrosis in a subject with HF, by administering a composition comprising at least one of BDNF, a TrkB agonist and a βAR-blocker, or a regulator thereof. A number of methods for evaluation of cardiac collagen deposition are known in the art, and are summarized in de Jong, S et al. (de Jong, S et al. Monitoring cardiac fibrosis: a technical challenge. Neth Heart J. 2012 January; 20(1); 2012 January). These methods include invasive methods, such as histology, as well as non-invasive methods, such as measuring circulating biomarkers in the blood, and magnetic resonance imagery (MRI). A skilled artisan could choose the monitoring method of choice based on the situation.

In one embodiment, the method of the present invention comprises reducing, preventing, and/or reversing ventricular remodeling following a cardiac event, such as a myocardial infarction (MI), by administering a composition comprising at least one of BDNF, a TrkB agonist and a βAR-blocker, or a regulator thereof. Identifying and monitoring left ventricular remodeling following a cardiac event, for example by molecular imaging, is known in the clinical arts, and is summarized in Shirani, J et al. (Shirani, J et al. Cardiac molecular imaging to track left ventricular remodeling in heart failure. Journal of Nuclear Cardiology. 1 Aug. 2016).

The invention encompasses administration of a composition comprising at least one of BDNF, a TrkB agonist and a βAR-blocker, or a regulator thereof, to practice the methods of the invention. The skilled artisan would understand, based on the disclosure provided herein, how to formulate and administer BDNF. The skilled artisan would understand, based on the disclosure provided herein, how to formulate and administer the appropriate TrkB agonist. In addition, the skilled artisan would understand, based on the disclosure provided herein, how to formulate and administer the appropriate βAR-blocker. However, the present invention is not limited to any particular method of administration or treatment regimen.

Combination Therapy

In some embodiments, the composition comprising the at least one of BDNF, a TrkB agonist and a βAR-blocker, or a combination thereof, or a regulator thereof, may be combined with at least one other agent useful for treating or preventing HF. Examples of agents useful for treating or preventing HF include, but are not limited to, diuretics, angiotensin converting enzyme (ACE)-inhibitors, angiotensin II receptor blockers (ARBs), calcium-channel blockers, digoxin, and statins. In one embodiment, an additional therapeutic agent is administered to a subject in combination with a composition comprising the at least one of BDNF, a TrkB agonist and a βAR-blocker, or a regulator thereof, such that a synergistic therapeutic effect is produced. A "synergistic therapeutic effect" refers to a greater-than-additive therapeutic effect which is produced by a combination of two or more therapeutic agents, and which exceeds that which would otherwise result from individual administration of any therapeutic agent alone. Therefore, lower doses of the therapeutic agents may be used for treating or preventing HF, resulting in increased therapeutic efficacy and decreased side effects. In some embodiments, the agent is a phosphodiesterase 5 (PED5) inhibitor. Examples of PED5 inhibitors include, but are not limited to, sildenafil, vardenafil, and tadalafil.

Pharmaceutical Compositions

The compositions may comprise any form as would be understood by one skilled in the art. Non-limiting examples of forms include a liquid, a paste, a gel, a bar, a cake, a powder, a granulate, an effervescent tablet, a chewing gum, a tablet, a capsule, a lozenge, a fast melting tablet or wafer, a sublingual tablet or a spray. Such products can be manufactured using conventional methods practiced in the food and beverage industry, or in pharmaceutical industry.

Preferably, the composition comprising BDNF or BDNF regulator is a liquid, for example, a liquid solution prepared for injection, and the composition comprising the at least one TrkB agonist or TrkB agonist regulator is a liquid, for example, a liquid solution prepared for injection, and the composition comprising the at least one βAR-blocker or βAR-blocker regulator is a solid, for example, a tablet or a capsule. Alternatively, all the composition components are combined in a liquid, for example, a liquid solution prepared for injection. Means for the preparation of these molecules, and their pharmaceutically-acceptable formulation, are known in the art and may include small molecule synthesis, nucleic acid synthesis, polypeptide synthesis, and any conjugation steps necessary, as well as standard pharmaceutical formulation steps necessary to carry out the invention.

The invention encompasses the preparation and use of compositions comprising a composition useful for treatment of heart disease, disclosed herein as a composition comprising at least one of BDNF, a TrkB agonist and a βAR-blocker, or a regulator thereof. A skilled artisan would recognize, based on the disclosure herein, that the term BDNF encompasses full-length BDNF, a functional fragment of BDNF, an analog of BDNF, and a derivative of BDNF; it should be noted that a vector encoding BDNF, or a functional fragment thereof, may also be referred to as BDNF. A skilled artisan would recognize, based on the disclosure herein, that the TrkB agonist comprises agents that increase TrkB mRNA or protein expression, agents that increase TrkB signaling activity, agents that enhance BDNF mRNA or protein expression, agents that increase interaction between TrkB and its ligand BDNF (e.g., bivalent antibodies that bind TrkB and BDNF, fusion proteins with CDR combinations that bind TrkB and BDNF), and other agents. In addition, a skilled artisan would recognize, based on the disclosure herein, that the at least one βAR-blocker comprises agents that decrease βAR mRNA or protein expression, agents that decrease βAR signaling activity, agents that decrease cardiac responsiveness to catecholamines, and other agents. The composition components may be present in the composition in the form of a pharmaceutically acceptable salt, such as in combination with a pharmaceutically acceptable cation or anion, as is well known in the art.

In various embodiments, the compositions useful in the methods of the invention may be administered, by way of example, systemically or parenterally, such as, in oral formulations. In addition to the appropriate therapeutic composition, such compositions may contain pharmaceutically acceptable carriers and other ingredients known to enhance and facilitate drug administration.

The formulations of the compositions described herein may be prepared by any method known or hereafter developed in the art of pharmacology. In general, such preparatory methods include the step of bringing the at least one of BDNF, a TrkB agonist and a βAR-blocker, or a regulator thereof, into association with a carrier or one or more other accessory ingredients, and then, if necessary or desirable, shaping or packaging the product into a desired single- or multi-dose unit.

Although the descriptions of compositions provided herein are principally directed to compositions which are suitable for ethical administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and perform such modification with merely ordinary, if any, experimentation.

Compositions that are useful in the methods of the invention may be prepared, packaged, or sold in formulations suitable for oral, parenteral, intravenous, and other known routes of administration.

A composition of the invention may be prepared, packaged, or sold in bulk, as a single unit dose, or as a plurality of single unit doses. As used herein, a "unit dose" is a discrete amount of the composition comprising a predetermined amount of the at least one of BDNF, a TrkB agonist and a βAR-blocker, or a regulator thereof. The amount of the composition is generally equal to the dosage of the at least one of BDNF, a TrkB agonist and a βAR-blocker, or a regulator thereof, which would be administered to a subject or a convenient fraction of such a dosage such as, for example, one-half or one-third of such a dosage.

The relative amounts of the at least one of BDNF, a TrkB agonist and a βAR-blocker, or a regulator thereof, the pharmaceutically acceptable carrier, and any additional ingredients in a composition of the invention will vary, depending upon the identity, size, and condition of the subject treated and further depending upon the route by which the composition is to be administered. By way of example, the composition may comprise between 0.1% and 100% (w/w) of the at least one of BDNF, a TrkB agonist and a βAR-blocker, or a regulator thereof.

In addition to the at least one of BDNF, a TrkB agonist and a βAR-blocker, or a regulator thereof, a composition of the invention may further comprise one or more additional pharmaceutically active agents.

Controlled- or sustained-release formulations of a composition of the invention may be made using conventional technology.

A formulation of a composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the at least one inorganic nitrate, organic nitrate, inorganic nitrite, or organic nitrite. Other formulations suitable for oral administration include, but are not limited to, a powdered or granular formulation, an aqueous or oily suspension, an aqueous or oily solution, or an emulsion.

A tablet comprising the at least one of BDNF, a TrkB agonist and a βAR-blocker, or a regulator thereof, may, for example, be made by compressing or molding the at least one of BDNF, a TrkB agonist and a βAR-blocker, or a regulator thereof, optionally with one or more additional ingredients. Compressed tablets may be prepared by compressing, in a suitable device, the active ingredient(s) in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient(s), a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient(s). By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide a pharmaceutically elegant and palatable preparation.

Hard capsules comprising the active ingredient(s) may be made using a physiologically degradable composition, such as gelatin. Such hard capsules comprise the at least one of BDNF, a TrkB agonist and a βAR-blocker, or a regulator thereof, and may further comprise additional ingredients including, for example, an inert solid diluent such as calcium carbonate, calcium phosphate, or kaolin.

Soft gelatin capsules comprising the active ingredient(s) may be made using a physiologically degradable composition, such as gelatin. Such soft capsules comprise the at least one of BDNF, a TrkB agonist and a βAR-blocker, or a regulator thereof, which may be mixed with water or an oil medium such as peanut oil, liquid paraffin, or olive oil.

Liquid formulations of a composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient(s) in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the at least one of BDNF, a TrkB agonist and a βAR-blocker, or regulator thereof, in aqueous or oily solvents may be prepared in substantially the same manner as liquid suspensions, the primary difference being that the active ingredient is dissolved, rather than suspended in the solvent. Liquid solutions of the composition of the invention may comprise each of the components described with regard to liquid suspensions, it being understood that suspending agents will not necessarily aid dissolution of the active ingredient(s) in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a composition includes any route of administration characterized by physical breaching of a tissue of a subject and administration of the composition through the breach in the tissue. Parenteral administration thus includes, but is not limited to, administration of a composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, and intramuscular, intracisternal injection.

Formulations of a composition suitable for parenteral administration comprise the active ingredient(s) combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient(s) is provided in dry (i.e., powder or granular) form for reconstitution with a suitable vehicle (e.g., sterile pyrogen-free water) prior to parenteral administration of the reconstituted composition.

The compositions may be prepared, packaged, or sold in the form of a sterile injectable aqueous or oily suspension or solution. This suspension or solution may be formulated according to the known art, and may comprise, in addition to the at least one of BDNF, a TrkB agonist and a βAR-blocker, or regulator thereof, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient(s) in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A composition of the invention may be prepared, packaged, or sold in a formulation suitable for buccal administration. Such formulations may, for example, be in the form of tablets or lozenges made using conventional methods, and may, for example, contain 0.1 to 100% (w/w) of the active ingredient(s), the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient(s). Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compounds of the invention which may be administered to an animal, preferably a human, range in amount from about 0.01 mg to about 100 g per kilogram of body weight of the animal. The precise dosage administered will vary depending upon any number of factors, including, but not limited to, the type of animal and type of disease state being treated, the age of the animal and the route of administration. In some embodiments, the dosage of the compound will vary from about 1 mg to about 100 mg per kilogram of body weight of the animal. In other embodiments, the dosage will vary from about 1 μg to about 1 g per kilogram of body weight of the animal. The compound can be administered to an animal as frequently as two, three, four, five, six, seven or eight times daily, or it can be administered less frequently, such as once a day, one or more times a week, one or more times every two weeks, one or more times a month, or even less frequently, such as one or more times every several months or even one or more times a year. The frequency of the dose will be readily apparent to the skilled artisan and will depend upon any number of factors, such as, but not limited to, the type and severity of the disease being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Myocardial βAR Signaling Increases Myocardial BDNF and is Regulated by Myocardial GRK2

In order to determine if β1/β2 stimulation promotes BDNF cardiac autologous production, and to test whether this generation is sensitive to β1/β2 activity level, in vitro experiments were conducted using neonatal rat ventricular cardiomyocytes (NRVMs) infected with an Adenovirus (Ad) encoding for G protein coupled receptor kinase 2 (GRK2) to induce a chronic state of βAR desensitization. Ad-Lacz was used as control. After 12 hrs of stimulation with the βAR-agonist Isoproterenol (ISO, 5 nM) it was found that ISO stimulation of Ad-Lacz (control) cells resulted in a significant increase of BDNF expression levels (~1.3-fold, n=3, FIG. 1). FIG. 1 depicts immunoblots for BDNF and GAPDH, taken from neonatal rat ventricular cardiomyocytes (NRVMs). NRVMs were infected with an Adenovirus (Ad) encoding for LacZ (control). Infected NRVMs were stimulated for 12 hours with (Iso) or without (non-stimulated, Ns) the βAR agonist Isoproterenol (ISO, 5 nM) prior to harvesting for immunoblot analysis. ISO stimulation of Ad-Lacz (control) cells resulted in a significant increase of BDNF expression levels (~1.3-fold, n=3) compared to non-stimulated (Ns) control cells.

Figure 2:
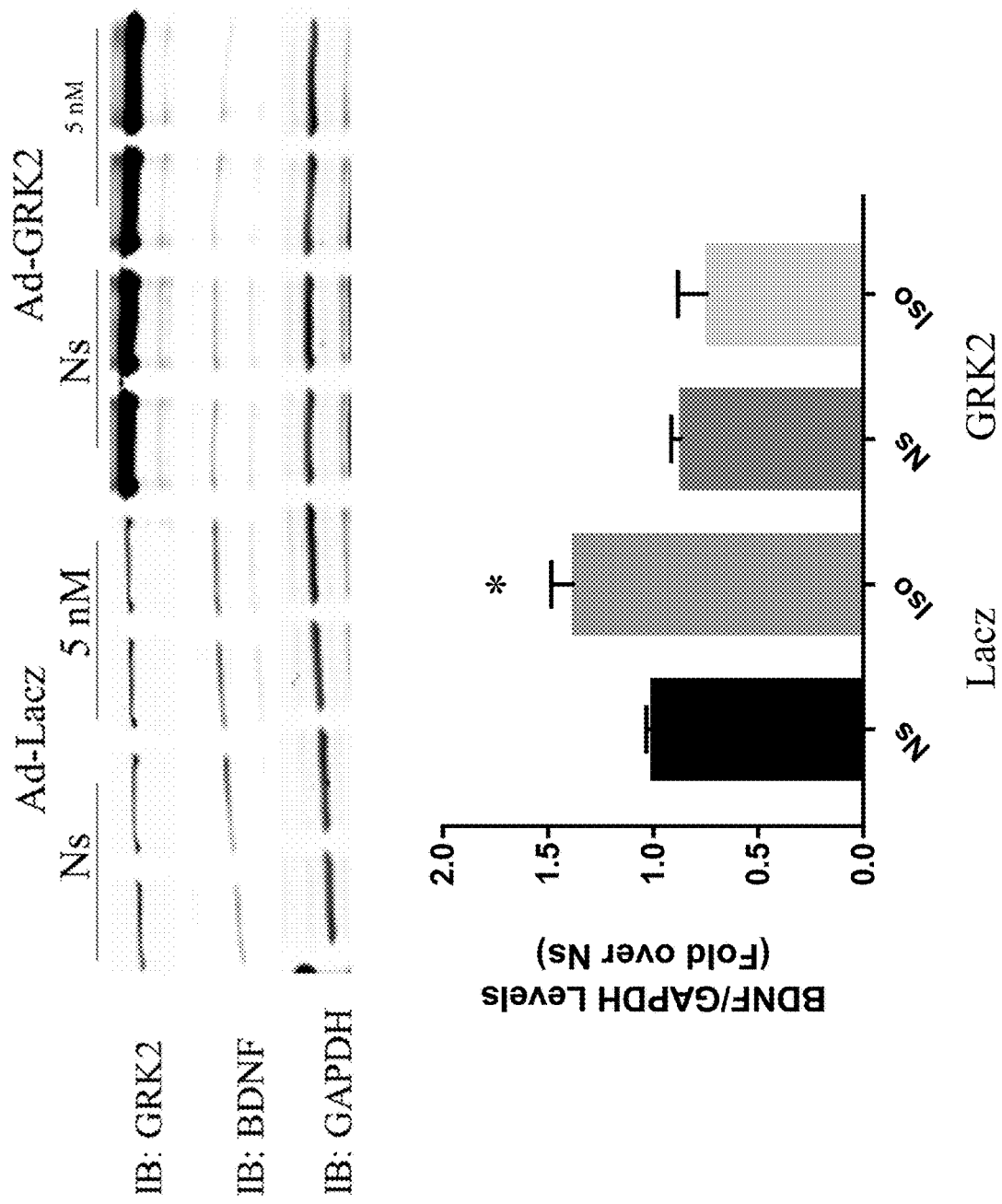
FIG. 2 depicts immunoblots for GRK2, BDNF, and GAPDH, taken from neonatal rat ventricular cardiomyocytes (NRVMs) infected with an Adenovirus (Ad) encoding for LacZ (control) or G protein coupled receptor kinase 2 (GRK2) to induce a chronic state of βAR desensitization. Infected NRVMs were stimulated for 12 hours with (Iso) or without (non-stimulated, Ns) the βAR agonist Isoproterenol (ISO, 5 nM) prior to harvesting for immunoblot analysis. The presence of high-levels of GRK2 in the cells abolished ISO-mediated production of BDNF.

This effect was abolished in the presence of high levels of GRK2 as in Ad-GRK2 transfected NRVMs (FIG. 2). FIG. 2 depicts immunoblots for GRK2, BDNF, and GAPDH, taken from neonatal rat ventricular cardiomyocytes (NRVMs) infected with an Adenovirus (Ad) encoding for LacZ (control) or G protein coupled receptor kinase 2 (GRK2) to induce a chronic state of βAR desensitization. Infected NRVMs were stimulated for 12 hours with (Iso) or without (non-stimulated, Ns) the βAR agonist Isoproterenol (ISO, 5 nM) prior to harvesting for immunoblot analysis. The presence of high-levels of GRK2 in the cells abolished ISO-mediated production of BDNF.

Figure 3:
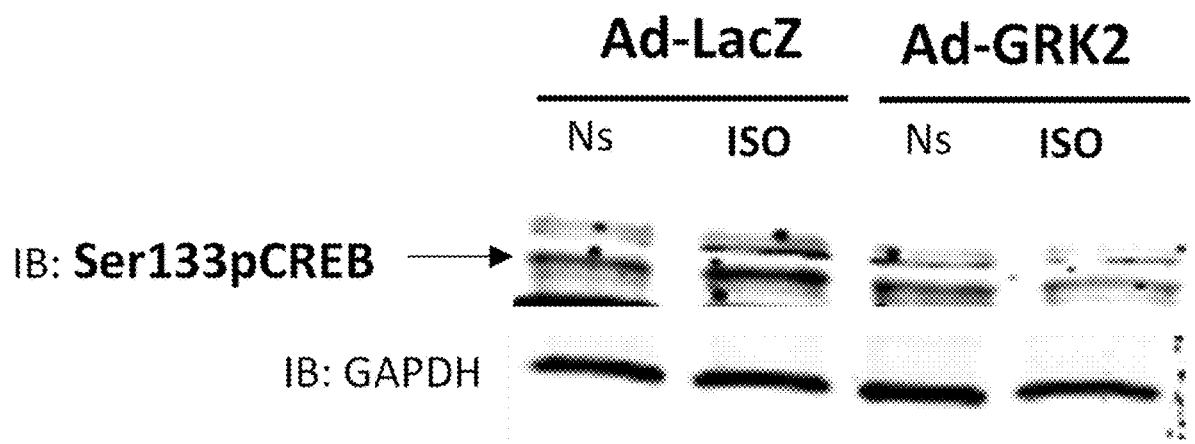
FIG. 3 depicts immunoblots for phospho-serine 133 CREB (Ser133pCREB) and GAPDH, taken from neonatal rat ventricular cardiomyocytes (NRVMs) infected with an Adenovirus (Ad) encoding for LacZ (control) or G protein coupled receptor kinase 2 (GRK2) to induce a chronic state of βAR desensitization. CREB is necessary for generating BDNF in any tissue (Finkbeiner S et al. Neuron. 1997; 19:1031-47), and phosphorylation at serine 133 is a critical step of CREB activation (Parker D et al. Mol Cell Biol. 1996; 16:694-703). The presence of high-levels of GRK2 in the cells abolished ISO-mediated production of Ser133pCREB.

Congruent with this, the activation of CREB that accounts for generating BDNF in any target tissue (Finkbeiner et al. Neuron. 1997; 19:1031-47) was evident in control (LacZ) cells (as indexed by the phosphorylation of Ser133, a critical step of CREB activation (Parker D et al. Mol Cell Biol. 1996; 16:694-703)), but not in Ad-GRK2 transfected NRVMs (FIG. 3). FIG. 3 depicts immunoblots for phospho-serine 133 CREB (Ser133pCREB) and GAPDH, taken from neonatal rat ventricular cardiomyocytes (NRVMs) infected with an Adenovirus (Ad) encoding for LacZ (control) or G protein coupled receptor kinase 2 (GRK2) to induce a chronic state of βAR desensitization. CREB is necessary for generating BDNF in any tissue (Finkbeiner et al. Neuron. 1997; 19:1031-47), and phosphorylation at serine 133 is a critical step of CREB activation (Parker et al. Mol Cell Biol. 1996; 16:694-703). The presence of high-levels of GRK2 in the cells abolished ISO-mediated production of Ser133pCREB.

Example 2: Cardiac GRK2 Overexpression Reduces BDNF Levels and Cardiac Function In Vivo after Induced Myocardial Infarction (MI)

Figure 4A:
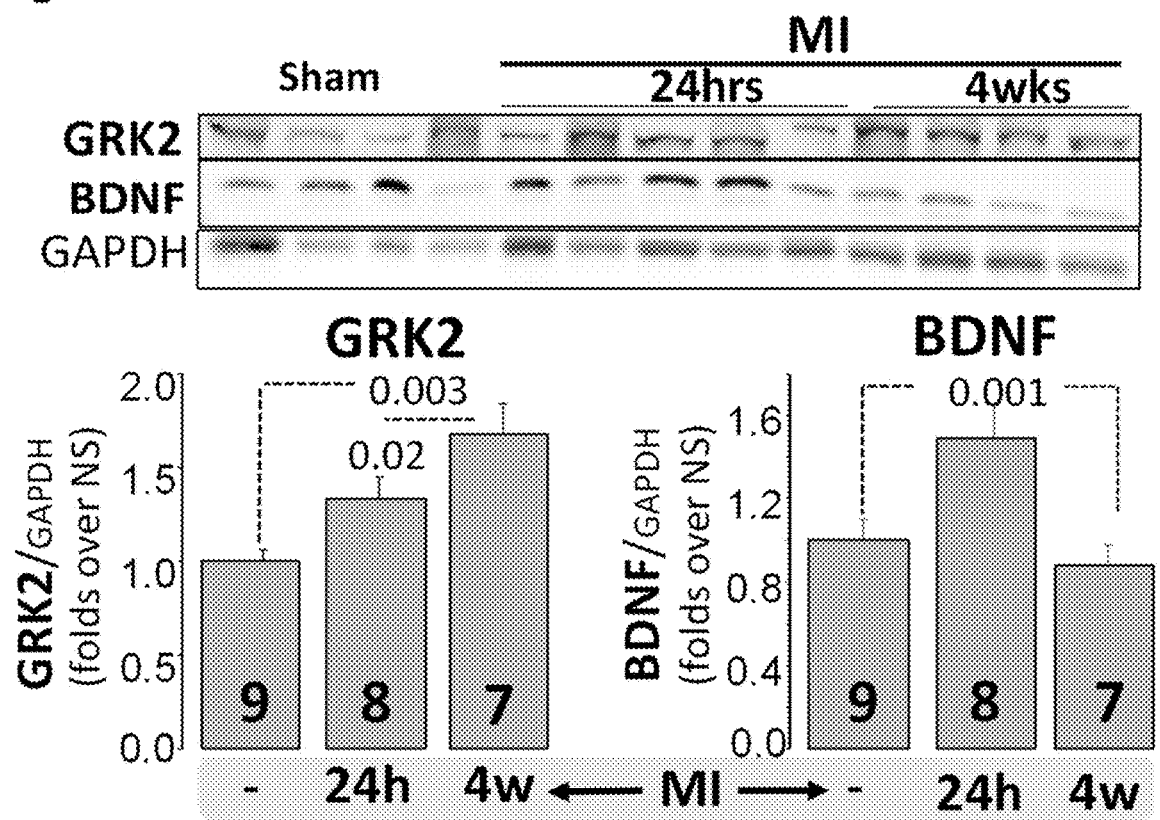
FIG. 4A through FIG. 4C, depicts experimental results.

To assess the in vivo relevance of these findings, MI was induced in control non-transgenic (NLC) mice, in cardiac-specific GRK2 overexpressing mice (TgGRK2) and in cardiac GRK2 knockout mice (cGRK2 KO). Four weeks after MI, left ventricle tissue analysis revealed that GRK2 was slightly, but not significantly upregulated after 24 hours after MI, whereas it was markedly elevated 4 weeks after the initial ischemic event. In parallel, cardiac BDNF expression was significantly elevated 24 hours after MI (when GRK2 was not significantly affected), but it plummeted to basal (pre-MI) values 4 weeks after MI when GRK2 peaked instead (FIG. 4A). FIG. 4A depicts immunoblots for GRK2, BDNF, and GAPDH, taken from left ventricle tissue of control non-transgenic (NLC) mice. Four weeks after induced myocardial infarction (MI), the analysis revealed that GRK2 was slightly, but not significantly upregulated after 24 hours following MI, whereas it was markedly elevated 4 weeks after the initial ischemic event. In parallel, cardiac BDNF expression was significantly elevated 24 hours after MI (when GRK2 was not significantly affected), but it plummeted to basal (pre-MI) values 4 weeks after MI when GRK2 peaked instead.

Figure 4B:
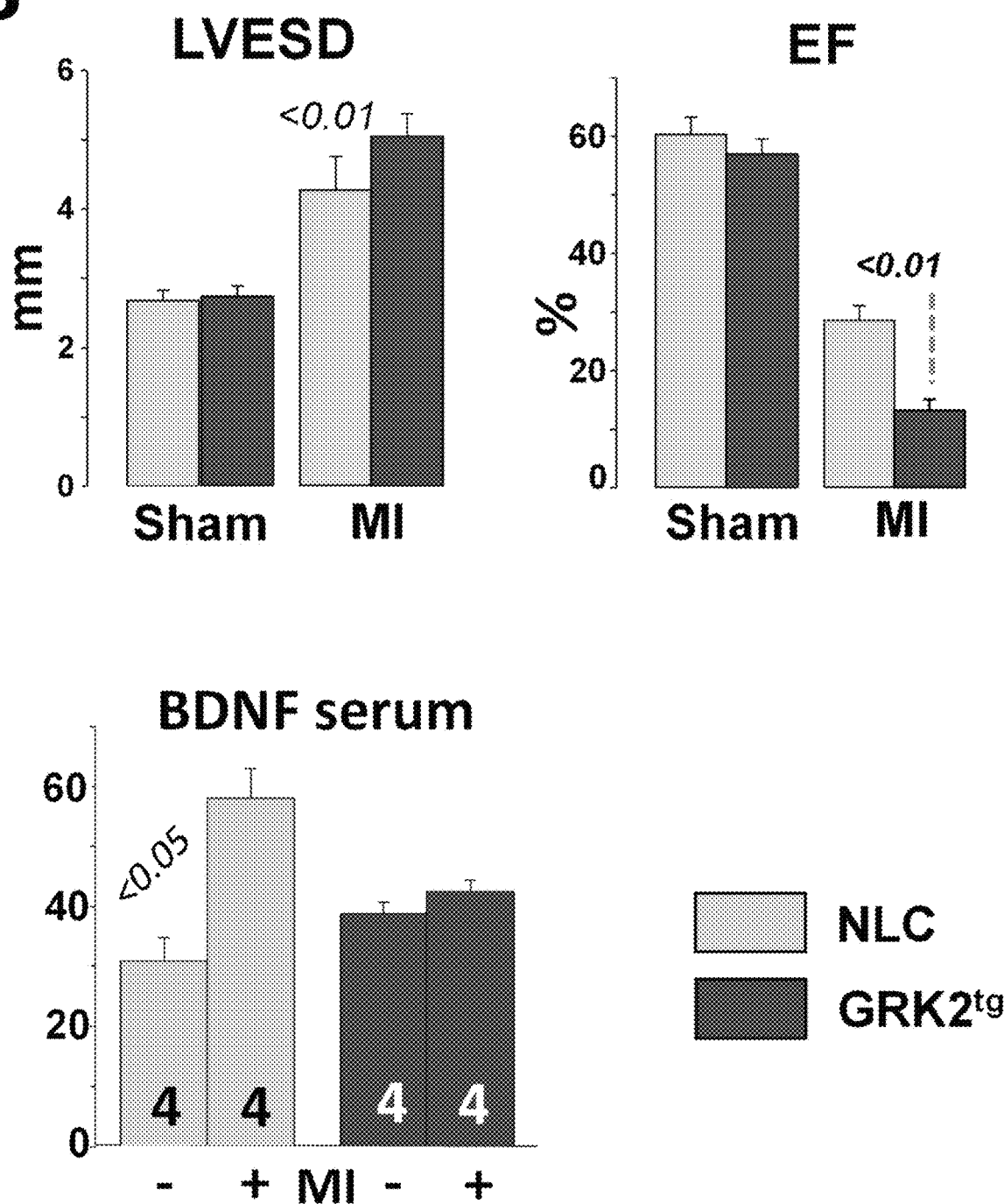

Echocardiographic analysis revealed that TgGRK2 mice presented with more severe cardiac dysfunction and adverse remodeling compared to NLC mice at 4 weeks after MI when chronic cardiac decompensation ensues (FIG. 4B). FIG. 4B depicts echocardiographic analyses (ejection fraction (EF), left ventricular end systolic dimension (LVESD)) of mouse hearts and serum levels of BDNF (BDNF serum) in control non-transgenic (NLC) mice (green bars) and in cardiac-specific GRK2 overexpressing mice (GRK2$^{tg}$) (red bars), taken 4 weeks after either MI or sham (control). GRK2$^{tg}$ mice presented with more severe cardiac dysfunction and adverse remodeling compared to NLC mice at 4 weeks after MI when chronic cardiac decompensation ensues. Moreover, whereas circulating BDNF levels increased in control (NCL) infarcted mice, serum BDNF was not elevated after MI in GRK2 transgenic (GRK2$^{tg}$) mice at this time point.

Figure 4C:
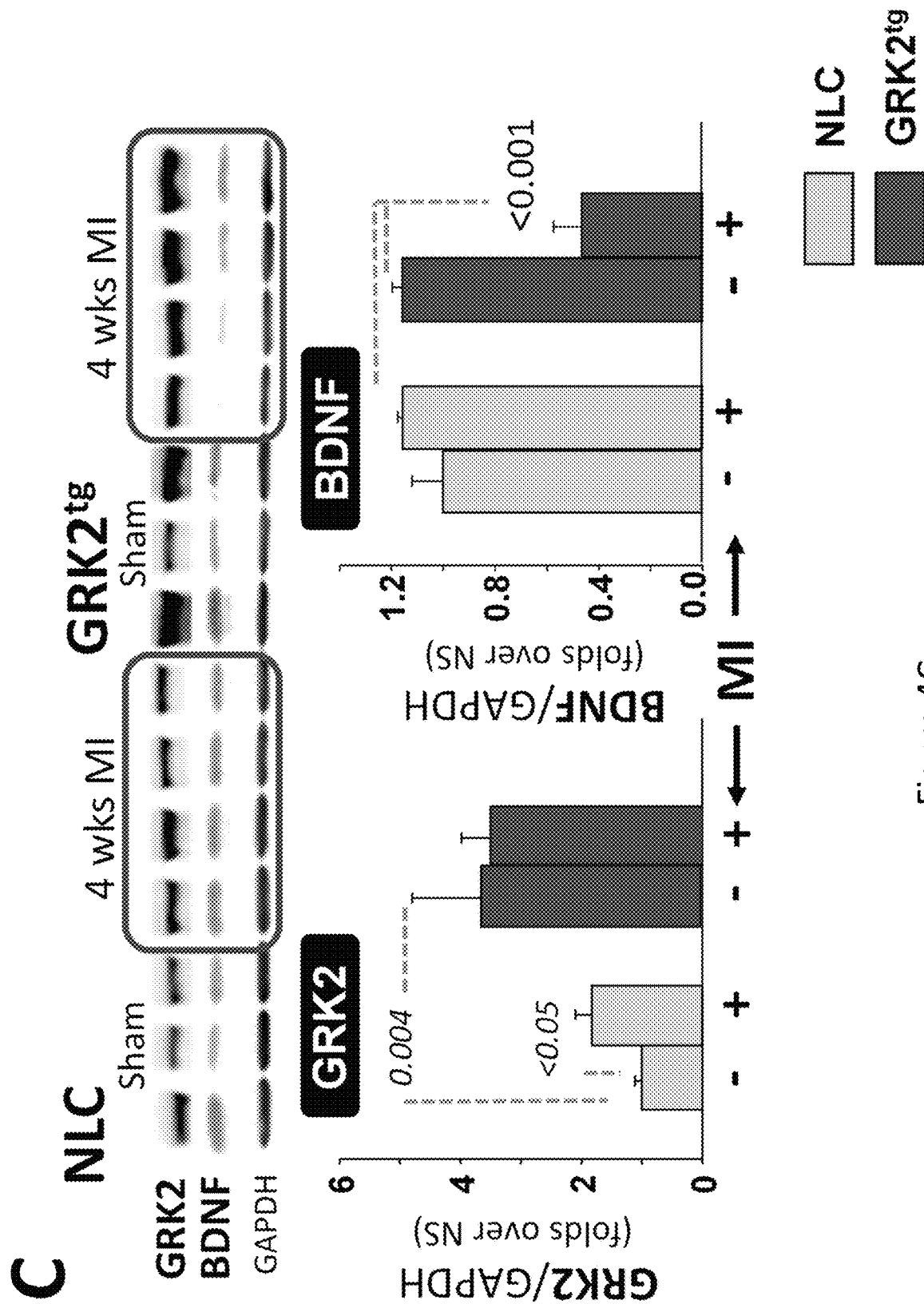

Importantly, BDNF was persistently elevated 4 weeks after MI in control (NLC) infarcted mice, but it dropped dramatically in infarcted GRK2tg mice in which GRK2 remained persistently elevated even after infarction (FIG. 4C). FIG. 4C depicts immunoblots for GRK2, BDNF, and GAPDH, taken from left ventricle tissue of control non-transgenic (NLC) mice or GRK2$^{tg}$ mice 4 weeks following sham or MI. Importantly, BDNF was persistently elevated 4 weeks after MI in control (NLC) infarcted mice, but it dropped dramatically in infarcted GRK2$^{tg}$ mice in which GRK2 remained persistently elevated even after infarction.

Example 3: Genetic Ablation of GRK2 Increases BDNF in Cardiac Lysates

Figure 5:
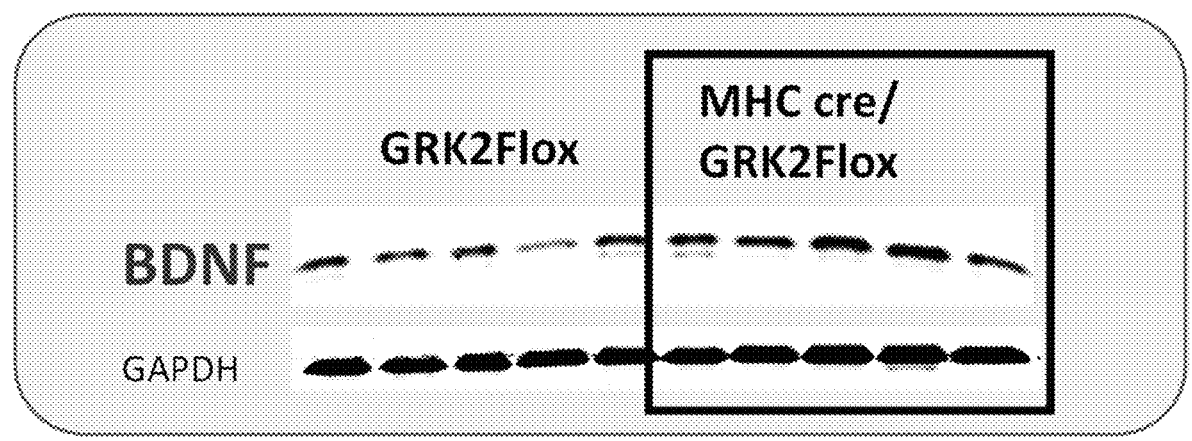
FIG. 5 depicts immunoblots for BDNF and GAPDH, taken from cardiac lysates of either control (NLC) mice, or cardiac-selective low-expressing GRK2 (cGRK2KO) mice. In cGRK2KO mice, BDNF levels were elevated at baseline, compared to NLC: 0.49±0.03 vs. 0.64±0.02 BDNF/GADPH ratios (p<0.05, n=5 each), and were more protected against ischemic injury. In fact, 4 weeks after MI, ejection fraction (% EF) was 22.11±5.8 in control (NLC) mice vs. 40.4±4.3 in cGRK2 KO mice, while end-systolic ventricular dimension (LVDs) was 4.71±0.24 vs. 3.54±0.26 mm in NLC and GRK2 KO mice, respectively (p<0.01 for both, n=13 each group).
Figure 5:
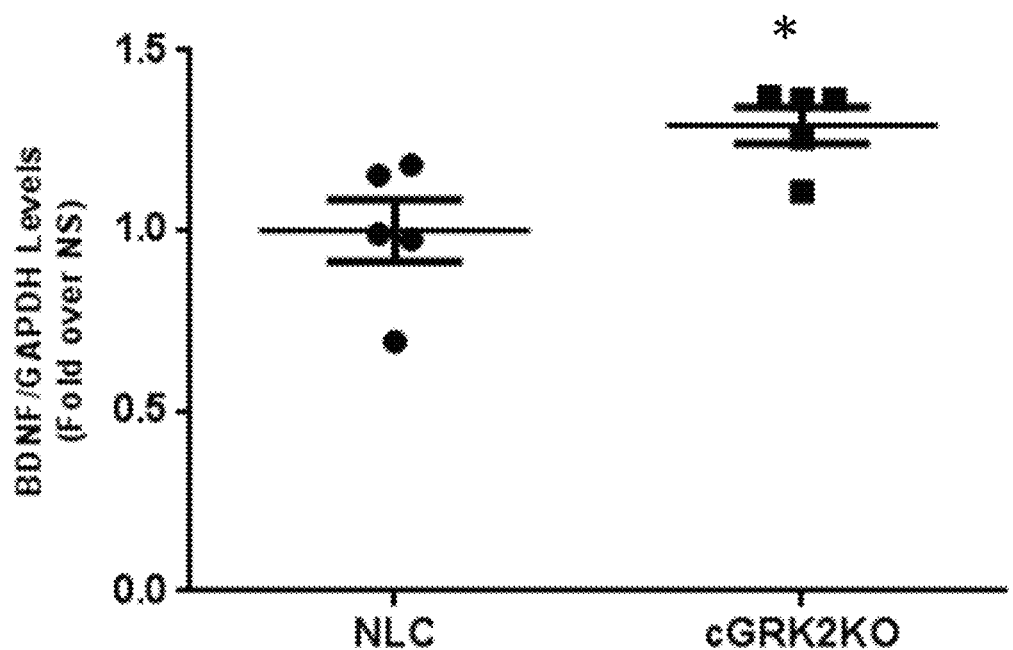

In stark contrast, in cardiac-selective low-expressing GRK2 (cGRK2 KO) mice, BDNF levels were already elevated at baseline compared to NLC: 0.49±0.03 vs. 0.64±0.02 BDNF/GADPH ratios (p<0.05, n=5 each, FIG. 5), and were more protected against ischemic injury. FIG. 5 depicts immunoblots for BDNF and GAPDH, taken from cardiac lysates of either control (NLC) mice, or cardiac-selective low-expressing GRK2 (cGRK2KO) mice. In cGRK2KO mice, BDNF levels were elevated at baseline, compared to NLC: 0.49±0.03 vs. 0.64±0.02 BDNF/GADPH ratios (p<0.05, n=5 each), and were more protected against ischemic injury. In fact, 4 weeks after MI, ejection fraction (% EF) was 22.11±5.8 in control (NLC) mice vs. 40.4±4.3 in cGRK2 KO mice, while end-systolic ventricular dimension (LVDs) was 4.71±0.24 vs. 3.54±0.26 mm in NLC and GRK2 KO mice, respectively (p<0.01 for both, n=13 each group). In fact, 4 weeks after MI, ejection fraction (% EF) was 22.11±5.8 in control (NLC) mice vs. 40.4±4.3 in cGRK2 KO mice, while end-systolic ventricular dimension (LVDs) was 4.71±0.24 vs. 3.54±0.26 mm in NLC and GRK2 KO mice, respectively (p<0.01 for both, n=13 each group). All together, these data suggest that βAR/BDNF is a new important signaling intersection in the heart, and that altered βAR activity directly affects myocardial BDNF generation and its potential therapeutic effects on the myocardium itself (autocrine effects) and on the neighboring tissues such as vessels and nerves serving the heart (paracrine effects).

Example 4: Loss of Adrenergic Fibers in GRK2 Overexpressing Mice Following Induced Myocardial Infarction (MI)

Figures 6A, 6B, 6C:
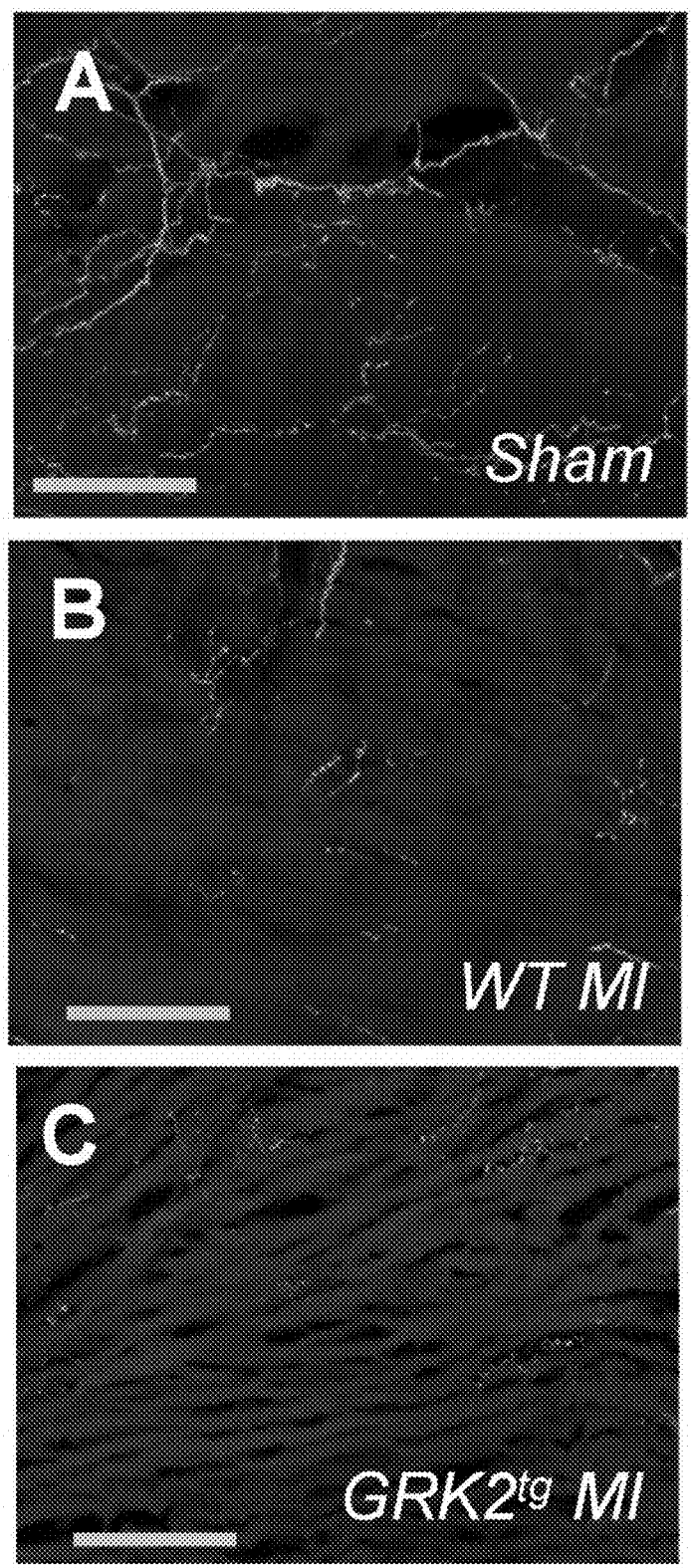
FIG. 6A through FIG. 6E, depicts experimental results.
Figures 6D, 6E:
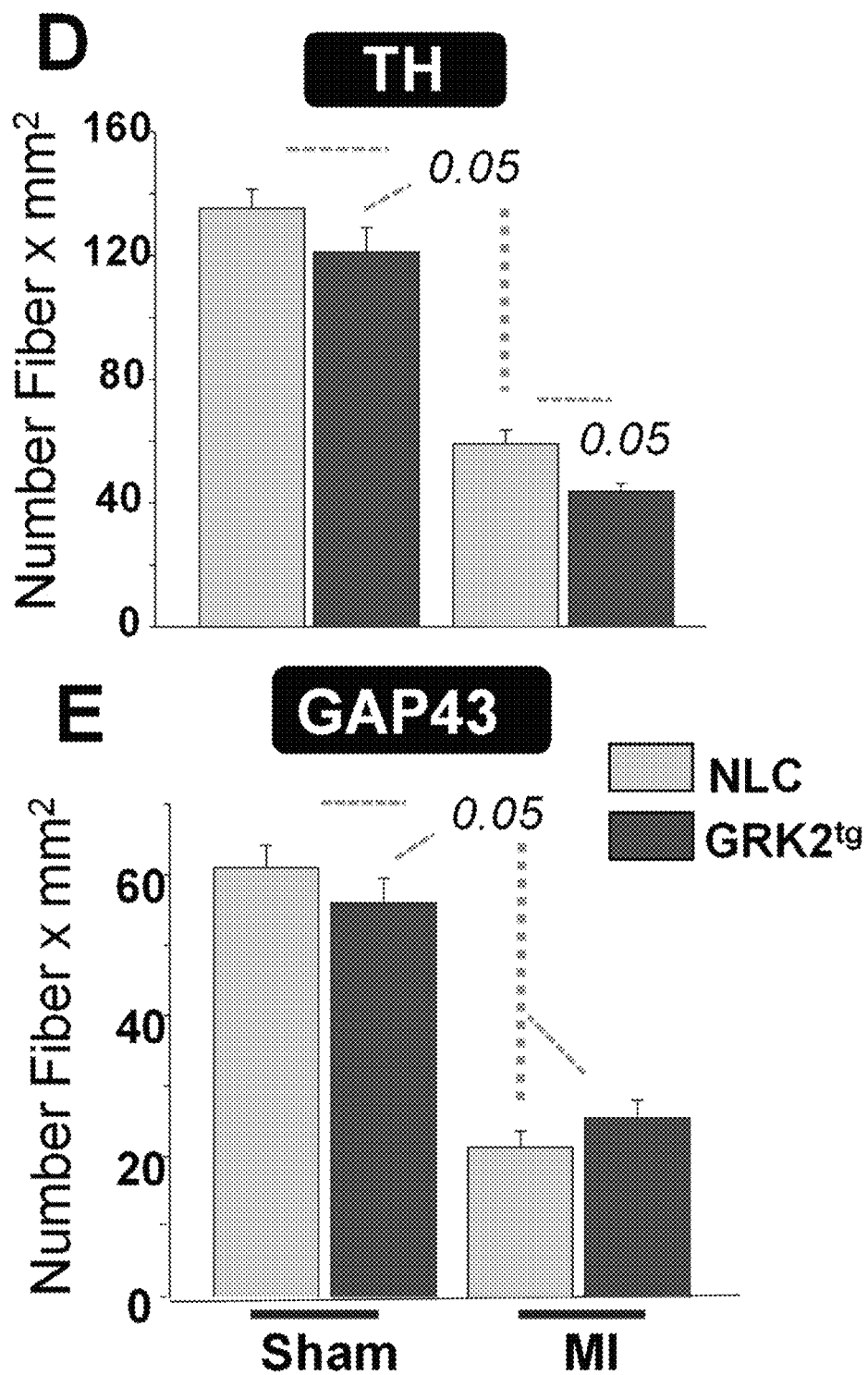

The position that βAR/BDNF is a new important signaling intersection in the heart is supported by additional data shown in FIG. 6 in which staining of planar sections of mouse left ventricle (LV) for tyrosine hydroxylase (TH), a marker of noradrenergic neurons (Melchitzky et al. Neuropsychopharmacology. 2000; 22:466-72. and Hoard J L, et al. Neuroscience. 2008; 156:129-42) and GAP-43, an integral membrane protein associated with the cytoplasmic surface of axonal growth cones (thus to axonal growth) are reported. In control (NLC) mice, myocardial infarction led to a marked reduction in both TH and GAP-43 staining. However, loss of adrenergic fibers was exacerbated in cGRK2tg that show reduced overall cardiac BDNF content 4 weeks after MI (FIG. 4).

Figure 7A:
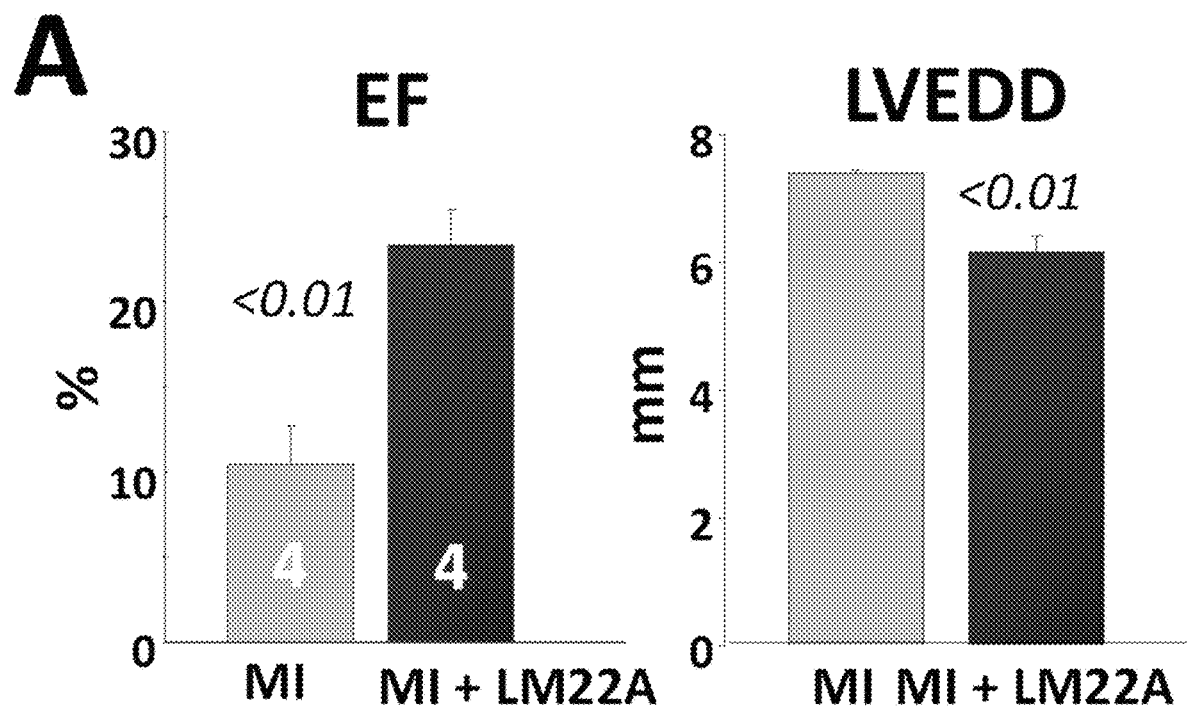
FIG. 7A through FIG. 7C, depicts experimental results.

Example 5: Treatment of Mice with LM22A-4, a Small-Molecule Agonist of TrkB, Improves Cardiac Structure and Function Following MI, and Increases BDNF Production Next, experiments were performed to determine whether highly selective TrkB agonists that mimic the effects of endogenous BDNF on sarcolemmal TrkB without binding to other neurotrophin-related receptors such as p75NTR (Massa S M, et al. J Clin Invest. 2010; 120:1774-85) would prevent LV dysfunction and adverse remodeling in mice with myocardial infarction. FIG. 7A depicts rescue of cardiac defects following FIG. 7A depicts rescue of cardiac defects following MI resulting from chronic infusion of LM22A-4, a specific agonist of TrkB (Massa S M, et al. J Clin Invest. 2010; 120:1774-85), at 0.2 mg/kg/day in saline, started 1 week after MI. The treatment prevented LV dysfunction and adverse remodeling 4 weeks after severe MI: % EF was 10.46±2.3 in untreated (vehicle treated) infarcted mice vs. 23.3±2.1 in LM22A-4 treated animals, while LVDs was 7.4±0.05 vs. 6.1±0.25 mm.

Figure 7B:
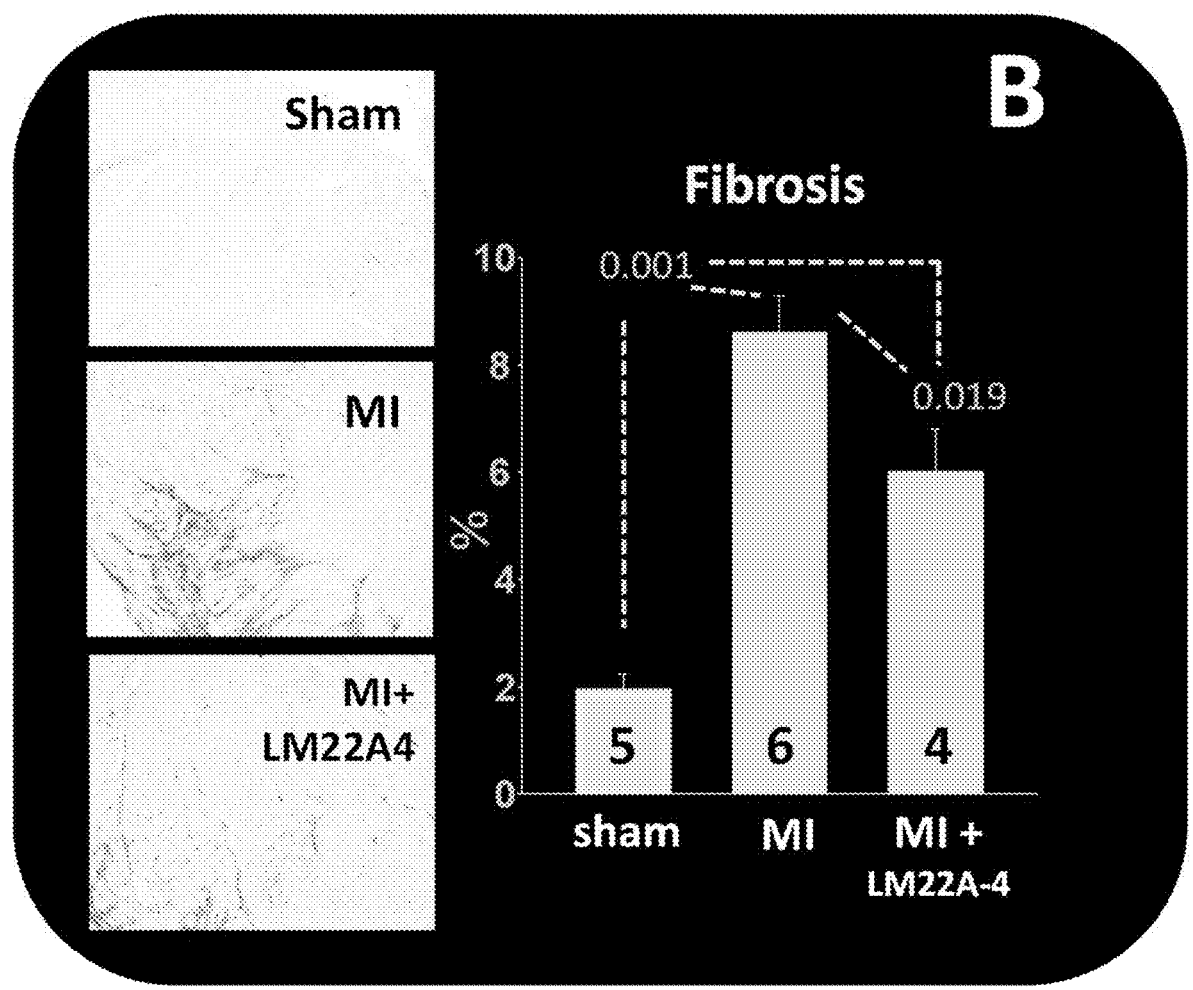

Overall fibrosis was lower in TrkB agonist-treated hearts (FIG. 7B). FIG. 7B depicts cardiac tissue sections and quantitation of fibrosis observed in sham, MI, and MI+LM22A-4 groups. Compared to the MI group without treatment, fibrosis was lower in TrkB agonist-treated hearts.

Figure 7C:
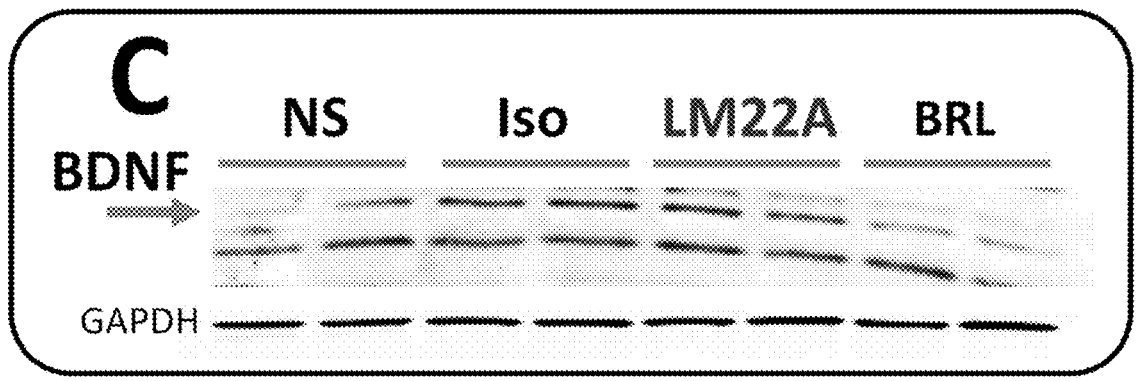

Importantly, chronic TrkB infusion did not alter heart rate, which actually tended to decline after LM22A-4 (525±10.3 in vehicle- vs. 494±17.8 bpm in TrkB agonist-treated MI mice). Of note, LM22A-4 induced myocardial BDNF in isolated control myocytes (FIG. 7C), lending support to the idea that cardiac sarcolemmal TrkB stimulation induces BDNF itself in the myocardium, and that this generation can contribute to TrkB agonists-afforded protection. FIG. 7C depicts immunoblots for BDNF and GAPDH from lysates taken from isolated control myocytes treated with NS, Iso, LM22A, or (33 agonist BRL 37344 (BRL). As shown, treatment with LM22A-4 induced myocardial BDNF in isolated control myocytes.

Example 6: TrkB Agonists Enhance eNOS Signaling

Figure 8:
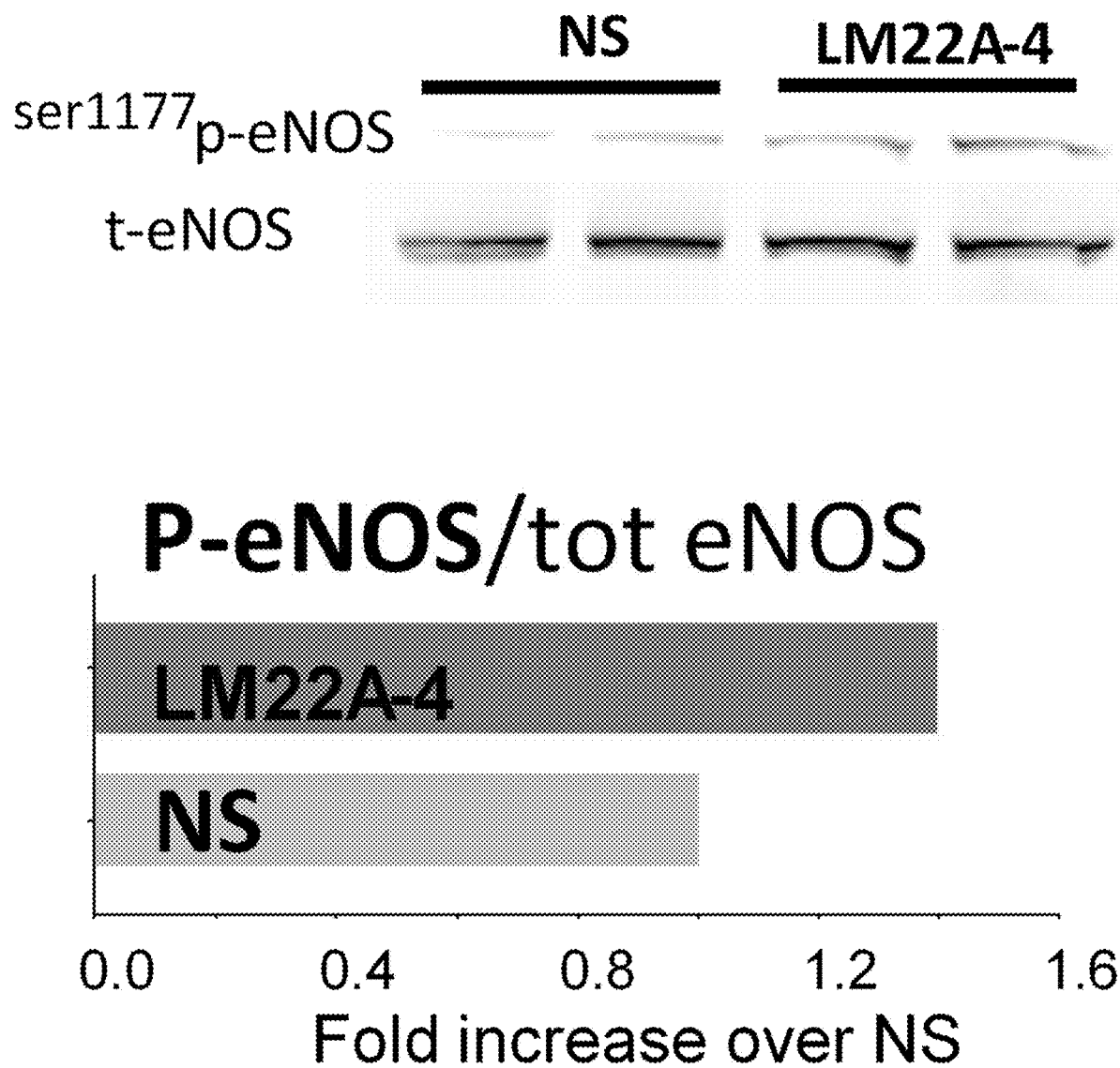
FIG. 8 depicts an immunoblot of eNOS phosphorylated at serine 1177 ($^{ser1177}$p-eNOS) and total eNOS (t-eNOS), taken from myocytes under control conditions (NS) and treated with LM22A-4. As shown, acute infusion of LM22A-4 (100 nM) activates eNOS in myocytes by phosphorylating the enzyme at serine 1177.

Another possible mechanism of protection granted by TrkB stimulation is eNOS stimulation. In fact, here it is reported, for the first time, that acute infusion of LM22A-4 (100 nM) activates eNOS in myocytes by phosphorylating the enzyme at serine 1177 (FIG. 8). Thus, it is plausible that TrkB agonists enhance eNOS signaling. FIG. 8 depicts an immunoblot of eNOS phosphorylated at serine 1177 ($^{ser1177}$p-eNOS) and total eNOS (t-eNOS), taken from myocytes under control conditions (NS) and treated with LM22A-4. As shown, acute infusion of LM22A-4 (100 nM) activates eNOS in myocytes by phosphorylating the enzyme at serine 1177.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or preventing heart failure in a subject in need thereof, comprising administering to said subject a therapeutically effective amount of a composition comprising a tyrosine receptor kinase B (TrkB) agonist, a wild type brain-derived neurotrophic factor (BDNF) polypeptide, and a β-adrenergic receptor (βAR) antagonist (βAR-blocker), wherein the TrkB agonist is at least one selected from the group consisting of N,N',N"-tris(2-hydroxyethyl)-1,3, 5-benzenetricarboxamide (LM22A-4), a pharmaceutically acceptable salt of LM22A-4, 7,8-dihydroxyflavone, a pharmaceutically acceptable salt of 7,8-dihydroxyflavone, a vector encoding TrkB, and a vector encoding an antisense nucleic acid molecule targeting GRK2; and wherein the heart failure is selected from the group consisting of impaired left ventricular ejection fraction ("systolic" heart failure), preserved ejection fraction (HFpEF or "diastolic" heart failure), heart failure associated with low BDNF level, heart failure associated with high cardiac fibrosis level, heart failure associated with ventricular remodeling following a cardiac event, heart failure associated with non-ischemic cardiomyopathy, heart failure associated with mitral valve regurgitation, heart failure associated with ischemic cardiomyopathy, heart failure associated with aortic regurgitation, and any combination thereof.

2. The method of claim 1, wherein said TrkB agonist is at least one selected from the group consisting of a vector encoding TrkB and a vector encoding an antisense nucleic acid molecule targeting GRK2.

3. The method of claim 1, wherein said βAR-blocker is at least one selected from the group consisting of Bisoprolol, Carvedilol, Carvedilol phosphate, Metoprolol Succinate, and Nebivolol.

4. A method of treating or preventing heart failure in a subject in need thereof, the method comprising administering to said subject a therapeutically effective amount of a composition comprising:

a) a tyrosine receptor kinase B (TrkB) agonist selected from the group consisting of N,N',N"-tris(2-hydroxyethyl)-1,3,5-benzenetricarboxamide (LM22A-4), a pharmaceutically acceptable salt of LM22A-4, 7,8-dihydroxyflavone, a pharmaceutically acceptable salt of 7,8-dihydroxyflavone, a vector encoding TrkB, a vector encoding an antisense nucleic acid molecule targeting GRK2, and any combination thereof;

b) a full-length wild type brain-derived neurotrophic factor (BDNF) polypeptide or a nucleic acid encoding a full-length wild type BDNF polypeptide; and c) a β-adrenergic receptor (βAR) antagonist (βAR-blocker) selected from the group consisting of Bisoprolol, Carvedilol, Carvedilol phosphate, Metoprolol Succinate, Nebivolol, and any combination thereof;

wherein the heart failure is selected from the group consisting of impaired left ventricular ejection fraction ("systolic" heart failure), preserved ejection fraction (HFpEF or "diastolic" heart failure), heart failure associated with low BDNF level, heart failure associated with high cardiac fibrosis level, heart failure associated with ventricular remodeling following a cardiac event, heart failure associated with non-ischemic cardiomyopathy, heart failure associated with mitral valve regurgitation, heart failure associated with ischemic cardiomyopathy, heart failure associated with aortic regurgitation, and any combination thereof.

* * * * *